(12) United States Patent
Hill

(10) Patent No.: US 10,980,671 B2
(45) Date of Patent: *Apr. 20, 2021

(54) SHUNT FOR VASCULAR FLOW ENHANCEMENT

(71) Applicant: Richard Allen Hill, Port Angeles, WA (US)

(72) Inventor: Richard A. Hill, Port Angeles, WA (US)

(73) Assignee: Richard Allen Hill, Port Angeles, WA (US)

( * ) Notice: Subject to any disclaimer, the term of this patent is extended or adjusted under 35 U.S.C. 154(b) by 455 days.

This patent is subject to a terminal disclaimer.

(21) Appl. No.: 15/760,622

(22) PCT Filed: Sep. 16, 2016

(86) PCT No.: PCT/US2016/052356
§ 371 (c)(1),
(2) Date: Mar. 15, 2018

(87) PCT Pub. No.: WO2017/049248
PCT Pub. Date: Mar. 23, 2017

(65) Prior Publication Data
US 2019/0060118 A1 Feb. 28, 2019

Related U.S. Application Data

(60) Provisional application No. 62/219,592, filed on Sep. 16, 2015.

(51) Int. Cl.
*A61F 9/007* (2006.01)
*A61F 9/00* (2006.01)
*A61B 90/20* (2016.01)

(52) U.S. Cl.
CPC ........ *A61F 9/00781* (2013.01); *A61F 9/0017* (2013.01); *A61B 90/20* (2016.02);
(Continued)

(58) Field of Classification Search
CPC ........................ A61F 9/00781; A61F 9/0017
See application file for complete search history.

(56) References Cited

U.S. PATENT DOCUMENTS 5,397,300 A 3/1995 Baerveldt
7,094,225 B2 8/2006 Tu
(Continued)

FOREIGN PATENT DOCUMENTS

WO WO 2010/093945 A2 8/2010
WO WO 2012/071476 A2 5/2012
WO WO 2014/145021 9/2014

OTHER PUBLICATIONS

Seyednejad et al., 2012, Biomacromol, 13:3650-3660. (Year: 2012).*

*Primary Examiner* — Ariana Zimbouski
(74) *Attorney, Agent, or Firm* — Grimes & Yvon LLP

(57) ABSTRACT

Drainage of body fluid from a first area of the body to a target area of the body can be accomplished by interconnecting an artificial non-blood fluid conduit with the venous and/or lymphatic system of the body. For example, an artificial non-blood fluid conduit can be inserted into the eye to fluidly interconnect the anterior chamber with a venous structure, such as an anterior ciliary vein, or lymphatic in a target location of the eye. The outflow end of the conduit can be positioned adjacent to and/or cannulated within the venous structure or lymphatic. Further, the conduit can optionally have an angiogenic material for stimulating growth of new blood vessels in the target location to fluidly interconnect the venous structure or lymphatic with the anterior chamber using the non-blood fluid conduit.

21 Claims, 18 Drawing Sheets

Specification includes a Sequence Listing.

(52) U.S. Cl.
CPC ............... *A61F 2210/0004* (2013.01); *A61F 2250/0031* (2013.01); *A61F 2250/0067* (2013.01)

(56) References Cited

U.S. PATENT DOCUMENTS

| | | |
|---|---|---|
| 7,163,543 B2 | 1/2007 | Smedley |
| 7,273,475 B2 | 9/2007 | Tu |
| 7,331,984 B2 | 2/2008 | Tu |
| 7,431,710 B2 | 10/2008 | Tu |
| 7,488,303 B1 | 2/2009 | Haffner |
| 7,708,711 B2 | 5/2010 | Tu |
| 7,867,186 B2 | 1/2011 | Haffner |
| 7,879,001 B2 | 2/2011 | Haffner |
| 7,879,079 B2 | 2/2011 | Tu |
| 7,951,155 B2 | 5/2011 | Smedley |
| 8,007,459 B2 | 8/2011 | Haffner |
| 8,337,445 B2 | 12/2012 | Tu |
| 8,506,515 B2 | 8/2013 | Burns |
| 8,617,094 B2 | 12/2013 | Smedley |
| 8,758,290 B2 | 6/2014 | Horvath |
| 8,882,781 B2 | 11/2014 | Smedley |
| 9,155,654 B2 | 10/2015 | Tu |
| 9,173,775 B2 | 11/2015 | Haffner |
| 9,220,632 B2 | 12/2015 | Smedley |
| 9,301,875 B2 | 4/2016 | Tu |
| 9,655,780 B2 * | 5/2017 | Hill .................. A61F 9/0017 |
| 2005/0049578 A1 | 3/2005 | Tu |
| 2007/0141116 A1 | 6/2007 | Pinchuk et al. |
| 2007/0293872 A1 | 12/2007 | Peyman |
| 2010/0234790 A1 | 9/2010 | Tu et al. |
| 2011/0238075 A1 | 9/2011 | Clauson |

* cited by examiner

Sequence annotation (Features)
Feature key            Positions(s)   Length    Description
Molecule Processing
Signal peptide         1-26           26        Ref.22  Ref.23  Ref.24
Chain                  27-232         206       Vascular endothelial
                                                growth factor A

*FIG. 9A*

SEQ ID NO:1                                        Length       Mass(Da)
Isoform VEGF206 [UniParc].          FASTA          232          27,042
Last modified November 16, 2001, Version 2
Checksum: FB49F364446F4D01
Vascular endothelial growth factor A precursor – Homo sapiens (Human)
```
         10         20         30         40         50
    MNFLLSWVHW SLALLLYLHH AKWSQAAPMA EGGGQNHHEV VKFMDVYQRS
         60         70         80         90        100
    YCHPIETLVD IFQEYPDEIE YIFKPSCVPL MRCGGCCNDE GLECVPTEES
        110        120        130        140        150
    NITMQIMRIK PHQGQHIGEM SFLQHNKCEC RPKKDRARQE KKSVRGKGKG
        160        170        180        190        200
    QKRKRKKSRY KSWSVYVGAR CCLMPWSLPG PHPCGPCSER RKHLFVQDPQ
        210        220        230
    TCKCSCKNTD SPCKARQLEL NERTCRCDKP RR
```

*FIG. 9B*

SEQ ID NO:2                                        Length       Mass(Da)
Isoform VEGF189 [UniParc].          FASTA          215          25,173
Checksum: 7B9759AD5971FF33
```
         10         20         30         40         50
    MNFLLSWVHW SLALLLYLHH AKWSQAAPMA EGGGQNHHEV VKFMDVYQRS
         60         70         80         90        100
    YCHPIETLVD IFQEYPDEIE YIFKPSCVPL MRCGGCCNDE GLECVPTEES
        110        120        130        140        150
    NITMQIMRIK PHQGQHIGEM SFLQHNKCEC RPKKDRARQE KKSVRGKGKG
        160        170        180        190        200
    QKRKRKKSRY KSWSVPCGPC SERPKHLFVQ DPQTCKCSCK NTDSRCKARQ
        210
    LELNERTCPC DKPRR
```

*FIG. 9C*

SEQ ID NO:3                                      Length      Mass(Da)
Isoform VEGF183 [UniParc].          FASTA        209         24,422
Checksum: F01CCEACD945D6CA
         10          20          30          40          50
    MNFLLSWVHW  SLALLLYLHH  AKWSQAAPMA  EGGGQNHHEV  VKFMDVYQRS
         60          70          80          90         100
    YCHPIETLVD  IFQEYPDEIE  YIFKPSCVPL  MRCGGCCNDE  GLECVPTEES
        110         120         130         140         150
    NITMQIMRIK  PHQGQHIGEM  SFLQHNKCEC  RPKKDRARQE  KKSVRGKGKG
        160         170         180         190         200
    QKRKRKKSRP  CGPCSERPKH  LFVQDPQTCK  CSCKNTDSRC  KARQLELNER

TCRCDKPRR

FIG. 9D

SEQ ID NO:4                                      Length      Mass(Da)
Isoform VEGF165 (VEGF) [UniParc].   FASTA        191         22,314
Checksum: CCE57097DD3779BD
         10          20          30          40          50
    MNFLLSWVHW  SLALLLYLHH  AKWSQAAPMA  EGGGQNHHEV  VKFMDVYQRS
         60          70          80          90         100
    YCHPIETLVD  IFQEYPDEIE  YIFKPSCVPL  MRCGGCCNDE  GLECVPTEES
        110         120         130         140         150
    NITMQIMRIK  PHQGQHIGEM  SFLQHNKCEC  RPKKDRARQE  NPCGPCSERR
        160         170         180         190
    KHLFVQDPQT  CKCSCKNTDS  RCKARQLELN  ERTCRCDKPR  R

FIG. 9E

SEQ ID NO:5  
Isoform VEGF148 [UniParc].  FASTA  Length 174  Mass(Da) 20,218  
Checksum: AE88400CA7757644

```
         10         20         30         40         50
   MNFLLSWVHW SLALLLYLHH AKWSQAAPMA EGGGQNHHEV VKFMDVYQRS
         60         70         80         90        100
   YCHPIETLVD IFQEYPDEIE YIFKPSCVPL MRCGGCCNDE GLECVPTEES
        110        120        130        140        150
   NITMQIMRIK PHQGQHIGEM SFLQHNKCEC RPKKDRARQE NPCGPCSERR
        160        170
   KHLFVQDPQT CKCSCKNTDS RCKM
```

FIG. 9F

SEQ ID NO:6  
Isoform VEGF145 [UniParc].  FASTA  Length 171  Mass(Da) 20,064  
Checksum: D02ECA735FF6E9F8

```
         10         20         30         40         50
   MNFLLSWVHW SLALLLYLHH AKWSQAAPMA EGGGQNHHEV VKFMDVYQRS
         60         70         80         90        100
   YCHPIETLVD IFQEYPDEIE YIFKPSCVPL MRCGGCCNDE GLECVPTEES
        110        120        130        140        150
   NITMQIMRIK PHQGQHIGEM SFLQHNKCEC RPKKDRAPQE KKSVRGKGKG
        160        170
   QKRKRKKSRY KSWSVCDKPR R
```

FIG. 9G

SEQ ID NO:7  
Isoform VEGF165B [UniParc].  FASTA  Length 191  Mass(Da) 22,259  
Checksum: D25243E540AC798D

```
         10         20         30         40         50
   MNFLLSWVHW SLALLLYLHH AKWSQAAPMA EGGGQNHHEV VKFMDVYQRS
         60         70         80         90        100
   YCHPIETLVD IFQEYPDEIE YIFKPSCVPL MRCGGCCNDE GLECVPTEES
        110        120        130        140        150
   NITMQIMRIK PHQGQHIGEM SFLQHNKCEC RPKKDRARQE NPCGPCSERR
        160        170        180        190
   KHLFVQDPQT CKCSCKNTDS RCKARQLELN ERTCPSLTRK D
```

FIG. 9H

SEQ ID NO:8
Isoform VEGF121 [UniParc].  FASTA  Length 147  Mass(Da) 17,219
Checksum: DDF4D6994249BED6

```
         10          20          30          40          50
  MNFLLSWVHW  SLALLLYLHH  AKWSQAAPMA  EGGGQNHHEV  VKFMDVYQRS
         60          70          80          90         100
  YCHPIETLVD  IFQEYPDEIE  YIFKPSCVPL  MRCGGCCNDE  GLECVPTEES
        110         120         130         140
  NITMQIMRIK  PHQGQHIGEM  SFLQHNKCEC  RPKKDRARQE  KCDKPRR
```

*FIG. 9I*

SEQ ID NO:9
Isoform VEGF111 [UniParc].  FASTA  Length 137  Mass(Da) 15,981
Checksum: 19682BB49381BE87

```
         10          20          30          40          50
  MNFLLSWVHW  SLALLLYLHH  AKWSQAAPMA  EGGGQNHHEV  VKFMDVYQRS
         60          70          80          90         100
  YCHPIETLVD  IFQEYPDEIE  YIFKPSCVPL  MRCGGCCNDE  GLECVPTEES
        110         120         130
  NITMQIMRIK  PHQGQHIGEM  SFLQHNKCEC  RCDKPRR
```

*FIG. 9J*

SEQ ID NO:10
Isoform L-VEGF165 [UniParc].  FASTA  Length 371  Mass(Da) 40,738
Checksum: 053E9CA56725C07B

```
         10          20          30          40          50
  MTDRQTDTAP  SPSYHLLPGR  PRTVDAAASR  GQGPEPAPGG  GVEGVGARGV
         60          70          80          90         100
  ALKLFVQLLG  CSRFGGAVVR  AGEAEPSGAA  RSASSGREEP  QPEEGEEEEE
        110         120         130         140         150
  KEEERGPQWR  LGARKPGSWT  GEAAVCADSA  PAARAPQALA  RASGRGGRVA
        160         170         180         190         200
  RRGAEESGPP  HSPSRRGSAS  RAGPGRASET  MNFLLSWVHW  SLALLLYLHH
        210         220         230         240         250
  AKWSQAAPMA  EGGGQNHHEV  VKFMDVYQRS  YCHPIETLVD  IFQEYPDEIE
        260         270         280         290         300
  YIFKPSCVPL  MRCGGCCNDE  GLECVPTEES  NITMQIMRIK  PHQGQHIGEM
        310         320         330         340         350
  SFLQHNKCEC  RPKKDRARQE  NPCGPCSERR  KHLFVQDPQT  CKCSCKNTDS
        360         370
  RCKARQLELN  ERTCRCDKPR  R
```

*FIG. 9K*

SEQ ID NO:11                                    Length      Mass(Da)
Isoform L-VEGF121 [UniParc].        FASTA        327        35,843
Checksum: 8D6F969601B2A9EF
            10          20          30          40          50
    MTDRQTDTAP  SPSYHLLPGR  RRTVDAAASR  GQGPEPAPGG  GVEGVGARGV
            60          70          80          90         100
    ALKLFVQLLG  CSRFGGAVVR  AGEAEPSGAA  RSASSGREEP  QPEEGEEEEE
           110         120         130         140         150
    KEEERGPQWR  LGARKPGSWT  GEAAVCADSA  PAARAPQALA  PASGRGGRVA
           160         170         180         190         200
    RPGAEESGPP  HSPSRRGSAS  RAGPGRASET  MNFLLSWVHW  SLALLLYLHH
           210         220         230         240         250
    AKWSQAAPMA  EGGGQNHHEV  VKFMDVYQRS  YCHPIETLVD  IFQEYPDEIE
           260         270         280         290         300
    YIFKPSCVPL  MRCGGCCNDE  GLECVPTEES  NITMQIMRIK  PHQGQHIGEM
           310         320
    SFLQHNKCEC  RPKKDRARQE  KCDKPRR

FIG. 9L

SEQ ID NO:12                                    Length      Mass(Da)
Isoform L-VEGF189 [UniParc].        FASTA        395        43,597
Checksum: 8ADF6524B1835A2D
            10          20          30          40          50
    MTDRQTDTAP  SPSYHLLPGR  RRTVDAAASR  GQGPEPAPGG  GVEGVGARGV
            60          70          80          90         100
    ALKLFVQLLG  CSRFGGAVVR  AGEAEPSGAA  RSASSGREEP  QPEEGEEEEE
           110         120         130         140         150
    KEEERGPQWR  LGARKPGSWT  GEAAVCADSA  PAARAPQALA  PASGRGGRVA
           160         170         180         190         200
    RPGAEESGPP  HSPSRRGSAS  RAGPGRASET  MNFLLSWVHW  SLALLLYLHH
           210         220         230         240         250
    AKWSQAAPMA  EGGGQNHHEV  VKFMDVYQRS  YCHPIETLVD  IFQEYPDEIE
           260         270         280         290         300
    YIFKPSCVPL  MRCGGCCNDE  GLECVPTEES  NITMQIMRIK  PHQGQHIGEM
           310         320         330         340         350
    SFLQHNKCEC  RPKKDRARQE  KKSVRGKGKG  QKRKPKKSRY  KSWSVPCGPC
           360         370         380         390
    SERRKHLFVQ  DPQTCKCSCK  NTDSRCKARQ  LELNERTCRC  DKPRR

FIG. 9M

```
SEQ ID NO:13                                         Length      Mass(Da)
Isoform L-VEGF206 [UniParc].        FASTA            412         45,467
Checksum: AC807D3F21528D35
          10         20         30         40         50
      MTDPQTDTAP SPSYHLLPGR RPTVDAAASR GQGPEPAPGG GVEGVGARGV
          60         70         80         90        100
      ALKLFVQLLG CSRFGGAVVR AGEAEPSGAA PSASSGPEEP QPEEGEEEEE
         110        120        130        140        150
      KEEERGPQWR LGARKPGSWT GEAAVCADSA PAAPAPQALA RASGRGGRVA
         160        170        180        190        200
      PPGAEESGPP HSPSRRGSAS RAGPGPASET MNFLLSWVHW SLALLLYLHH
         210        220        230        240        250
      AKWSQAAPMA EGGGQNHHEV VKFMDVYQRS YCHPIETLVD IFQEYPDEIE
         260        270        280        290        300
      YIFKPSCVPL MRCGGCCNDE GLECVPTEES NITMQIMRIK PHQGQHIGEM
         310        320        330        340        350
      SFLQHNKCEC RPKKDRARQE KKSVRGKGKG QKRKRKKSRY KSWSVYVGAR
         360        370        380        390        400
      CCLMPWSLPG PHPCGPCSER RKHLFVQDPQ TCKCSCKNTD SRCKARQLEL
         410
      NERTCRCDKP RR
```

*FIG. 9N*

| Sequence annotation (Features) | | | | | |
|---|---|---|---|---|---|
| Feature key | Position(s) | Length | Description | Graphical view | Feature identifier |
| Molecule processing | | | | | |
| Signal peptide | 1-21 | 21 | Potential | | |
| Chain | 22-207 | 186 | Vascular endothelial growth factor B | | PRO_0000023338 |

FIG. 10A

SEQ ID NO:14            Length    Mass(Da)
Isoform VEGF-B186 [UniParc].    FASTA    207     21,602
Last modified November 16, 2001. Version 2.
Checksum: EDE4B1C0DFDAD6BC

```
        10         20         30         40         50
 MSPLLRRLLL AALLQLAPAQ APVSQPDAPG HQRKVVSWID VYTRATCQPR
        60         70         80         90        100
 EVVVPLTVEL MGTVAKQLVP SCVTVQRCGG CCPDDGLECV PTGQHQVRMQ
       110        120        130        140        150
 ILMIRYPSSQ LGEMSLEEHS QCECRPKKKD SAVKPDRAAT PHHRPQPRSV
       160        170        180        190        200
 PGWDSAPGAP SPADITHPTP APGPSAHAAP STTSALTPGP AAAAADAAAS

SVAKGGA
```

FIG. 10B

SEQ ID NO:15            Length    Mass(Da)
Isoform VEGF-B167 [UniParc].    FASTA    188     21,261
Checksum: F04654D5A3727194

```
        10         20         30         40         50
 MSPLLRRLLL AALLQLAPAQ APVSQPDAPG HQRKVVSWID VYTRATCQPR
        60         70         80         90        100
 EVVVPLTVEL MGTVAKQLVP SCVTVQRCGG CCPDDGLECV PTGQHQVRMQ
       110        120        130        140        150
 ILMIRYPSSQ LGEMSLEEHS QCECRPKKKD SAVKPDSPRF LCPRCTQHHQ
       160        170        180
 RPDPRTCRPR CRRRSFLRCQ GRGLELNPDT CPCRKLRR
```

FIG. 10C

| Sequence annotation (Features) | | | | | |
|---|---|---|---|---|---|
| Feature key | Positions(s) | Length | Description | Graphical view | Feature identifier |
| Molecule processing | | | | | |
| Signal peptide | 1-31 | 31 | Ref 9 Ref 10 | | |
| Propeptide | 32-111 | 80 | Or 102 | | PRO_0000023400 |
| Chain | 112-227 | 116 | Vascular endothelial growth factor C | | PRO_0000023401 |
| Propeptide | 228-419 | 192 | | | PRO_0000023402 |

FIG. 11A

SEQ ID NO:16  
P49767 [UniParc].  FASTA  Length 419  Mass(Da) 46,883  
Last modified October 1, 1996. Version 1.  
Checksum: 9F598719DB3E014F

```
            10         20         30         40         50
    MHLLGFFSVA CSLLAAALLP GPPEAPAAAA AFESGLDLSD AEPDAGEATA
            60         70         80         90        100
    YASKDLEEQL RSVSSVDELM TVLYPEYWKM YKCQLRKGGW QHNPEQANLN
           110        120        130        140        150
    SRTEETIKFA AAHYNTEILK SIDNEWRKTQ CMPREVCIDV GKEFGVATNT
           160        170        180        190        200
    FFKPPCVSVY RCGGCCNSEG LQCMNTSTSY LSKTLFEITV PLSQGPKPVT
           210        220        230        240        250
    ISFANHTSCR CMSKLDVYPQ VHSIIRRSLP ATLPQCQAAN KTCPTNYMWN
           260        270        280        290        300
    NHICRCLAQE DFMFSSDAGD DSTDGFHDIC GPNKELDEET CQCVCRAGLR
           310        320        330        340        350
    PASCGPHKEL DPNSCQCVCK NKLFPSQCGA NREFDENTCQ CVCKRTCPRN
           360        370        380        390        400
    QPLNPGKCAC ECTESPQKCL LKGKKFHHQT CSCYRRPCTN RQKACEPGFS
           410
    YSEEVCRCVP SYWKRPQMS
```

FIG. 11B

| Sequence annotation (Features) | | | | | |
|---|---|---|---|---|---|
| Feature key | Positions(s) | Length | Description | Graphical view | Feature identifier |
| Molecule processing | | | | | |
| Signal peptide | 1-21 | 21 | Potential | | |
| Propeptide | 22-88 | 67 | Or 99 | | PRO_0000023408 |
| Chain | 89-205 | 117 | Vascular endothelial growth factor D | | PRO_0000023409 |
| Propeptide | 206-354 | 149 | | | PRO_0000023410 |

*FIG. 12A*

```
SEQ ID NO:17                                    Length      Mass(Da)
O43915 [UniParc]                  FASTA         354         40,444
Last modified June 1, 1998. Version 1
Checksum: 2048D769D735173E
             10         20         30         40         50
       MYREWVVVNV FMMLYVQLVQ GSSNEHGPVK RSSQSTLERS EQQIRAASSL
             60         70         80         90        100
       EELLRITHSE DWKLWRCRLP LKSFTSMDSR SASHRSTPFA ATFYDIETLK
            110        120        130        140        150
       VIDEEWQRTQ CSPRETCVEV ASELGKSTNT FFKPPCVNVF RCGGCCNEES
            160        170        180        190        200
       LICMNTSTSY ISKQLFEISV PLTSVPELVP VKVANHTGCK CLPTAPRHPY
            210        220        230        240        250
       SIIRRSIQIP EEDRCSHSKK LCPIDMLWDS NKCKCVLQEE NPLAGTEDHS
            260        270        280        290        300
       HLQEPALCGP HMMFDEDRCE CVCKTPCPKD LIQHPKNCSC FECKESLETC
            310        320        330        340        350
       CQKHKLFHPD TCSCEDRCPF HTPPCASGKT ACAKHCRFPK EKRAAQGPHS
       RKNP
```

*FIG. 12B*

SHUNT FOR VASCULAR FLOW ENHANCEMENT

CROSS-REFERENCE TO RELATED APPLICATIONS

This application claims priority to and the benefit of U.S. Patent Application No. 62/219,592, filed on Sep. 16, 2015, the entirety of which is incorporated herein by reference.

CROSS-REFERENCE TO A SEQUENCE LISTING

A Sequence Listing is being submitted electronically via EFS in the form of a text file, created Sep. 12, 2016, and named 0928240029SeqList.txt (37,037 bytes), the contents of which are incorporated herein by reference in their entirety.

TECHNICAL FIELD

The present inventions relate to the enhancement of flow out of a first area using a venous structure of the body. For example, the present disclosure relates to, among other things, creating an artificial channel to permit aqueous flow from the anterior chamber to a venous structure in the eye to treat glaucoma. The present disclosure also relates to the use of such methods to create artificial flow pathways and/or repair flow pathways in the vascular system, including applications related to the heart or a vessel of the heart, an artificial kidney, the cerebral vascular system, and the venous and/or lymphatic vasculature. Some embodiments can facilitate the use of a medical device and improve its biointegration and connection to venous and/or lymphatic structures with which the medical device fluidly communicates.

BACKGROUND

Various treatments and therapies rely on the successful use of artificial fluid conduits, or shunts, with the human body. A shunt is a device which provides a hole or a passage allowing fluid to move from one part of the body to another. While it is important that the shunt is compatible with the surrounding tissues, the shunt will ideally also facilitate healing or therapy of the diseased tissue without interfering with or inhibiting the intended therapy.

As an example, the treatment of glaucoma can include implanting a fluid conduit within the eye in order to facilitate or perform the work of natural outflow pathways that drain aqueous humor from an anterior chamber of the eye to a location of lower pressure, thus relieving high intraocular pressure within the anterior chamber. Nevertheless, an ocular implant can have complications such as excessive scar tissue formation or blockage of the shunt. Accordingly, there remains a need for an implant or shunt which can facilitate fluid flow through blocked tissue areas such as the trabecular network of the eye while avoiding harmful complications.

Therapies other than ocular therapies also rely on relieving high fluid pressure in a vessel or otherwise transporting fluids using an artificial fluid conduit. Such therapies can also benefit from the devices and methods described herein.

BRIEF SUMMARY

In some embodiments, methods and apparatuses are provided herein for fluidly interconnecting blood vessels with non-blood artificial conduits.

For example, some embodiments of the methods and apparatuses disclosed herein can provide a manner of facilitating outflow of aqueous humor through a shunt from the anterior chamber to a location of lower pressure by interconnecting the shunt with a venous structure of the eye, such as an anterior ciliary vein, or lymphatic channel. Some embodiments can also be implemented to create new veins, using an angiogenic material, carried by the shunt or otherwise deposited onto or into the eye at the outflow end of the shunt, to create new vessels that fluidly interconnect and outflow end of the shunt with the venous structure, such as an anterior ciliary vein, or lymphatic channel. Further, according to some embodiments is the realization that any new vessel created with an angiogenic factor is not a natural outflow pathway.

According to some embodiments, a method can be performed to fluidly interconnect an intraocular implant, such as an intraocular shunt, with a venous structures and/or lymphatic channels (such as orbital lymphatic channels, lymphatics in extra-ocular muscles). The shunt can be inserted into a body using a delivery device. The shunt can comprise first and second end regions. The first end can be positioned in a target area, and the second end region can be positioned adjacent to the venous structure (e.g., on the surface of the eye or sclera under the conjunctiva). After the shunt is inserted properly positioned, the delivery device can be withdrawn from the body.

In some embodiments, the second end region (e.g., an outflow end) can be positioned adjacent to the anterior ciliary vein. In some embodiments, the second end region can be positioned outside of the sclera, adjacent to the anterior ciliary vein.

Further, whether positioned within or superficial to the sclera, the second end region can be cannulated or mechanically connected with the venous system. For example, whether positioned within or superficial to the sclera, the second end region can be cannulated or mechanically connected with the anterior ciliary vein.

Furthermore, whether positioned within or superficial to the sclera, the second end region can be cannulated or mechanically connected with the lymphatic system, such as one or more lymphatic structures or orbital lymphatics.

In some embodiments, the shunt can comprise an angiogenic material at either or both of its end regions and/or along its length. The angiogenic material can be coated onto the implant For example, the second end region can optionally comprise an angiogenic material. Thus, when the shunt is not mechanically connected or cannulated within the venous structure or lymphatic structure, angiogenic material can facilitate growth of new vessels that allow the second end region of the shunt to interconnect with the venous structure or lymphatic structure.

The connection between the shunt and the anterior ciliary vein can entirely exclude any fluid connection with the episcleral veins. In accordance with some embodiments disclosed herein is the realization that the episcleral veins of the eye are used as "natural aqueous outflow pathways" or aqueous humor drainage channels and that the anterior ciliary veins function solely to transport blood to and from the ciliary body and do not principally function to transport aqueous humor; accordingly, the anterior ciliary veins are not natural outflow pathways for aqueous humor.

Hitherto, no glaucoma treatment has used the anterior ciliary veins as a means for aqueous humor drainage. Thus, in some embodiments, the shunt can connect only to anterior ciliary veins (either by using an angiogenic material or through mechanical connection, such as cannulation), which is considered to be a non-natural outflow pathway. However, some embodiments of the methods disclosed herein can also include forming an outflow pathway to both episcleral veins and anterior ciliary veins. Accordingly, reference to connection between the shunt and an anterior ciliary vein can, in some embodiments, exclude any interconnection with an episcleral vein.

In some embodiments, the methods and apparatuses disclosed herein can be modified to provide means for release of angiogenic material from the implant or to a location adjacent to the implant outflow end when implanted in the eye. For example, the shunt or portion thereof can be constructed of, encased in, or coated with a resorbable material such as a material containing poly-e-caprolactone (PCL). In some embodiments, the resorbable material comprises PCL with heparin, collagen or poly-(hydroxymethyl-glycolide-co-ε-coprolactone) (PpHMGCL).

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIGS. 9A-9N describe amino acid sequences for isoforms of VEGF A.

FIGS. 10A-10C describe amino acid sequences for isoforms of VEGF B.

FIGS. 11A-11B describe an amino acid sequence for VEGF C.

FIGS. 12A-12B describe an amino acid sequence for VEGF D.

DETAILED DESCRIPTION

Figure 1:
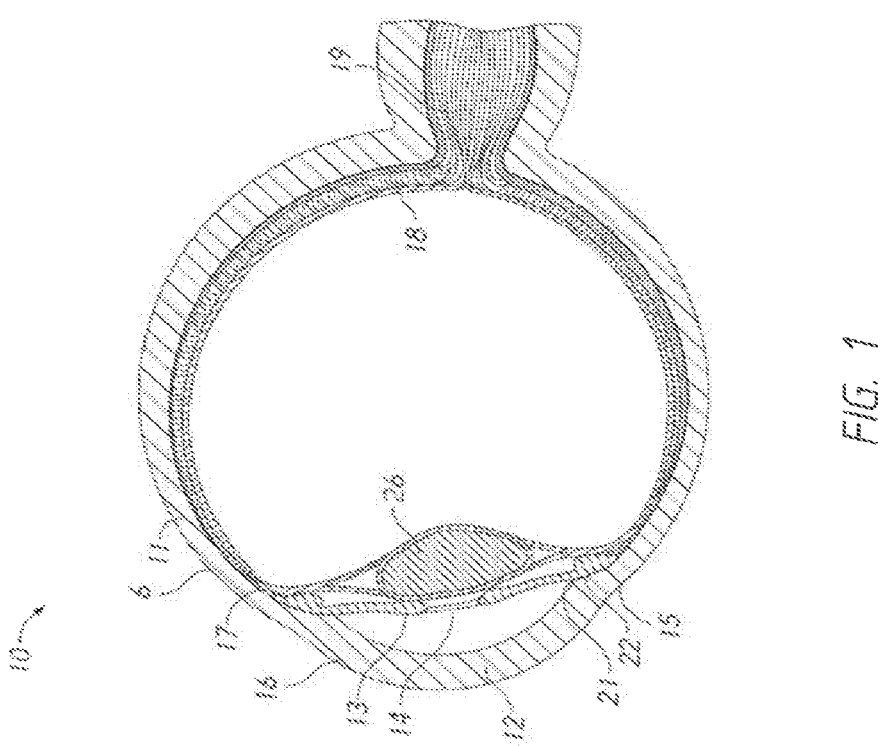
FIG. 1 is a cross-sectional view of an eye.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein.

Some embodiments disclosed herein provide devices and/or methods of interconnecting a non-blood fluid conduit with venous structures and/or lymphatic channels, which can be performed to relieve pressure and/or improve fluid flow from an area of higher pressure to an area of lower pressure. In some embodiments, the non-blood fluid conduit can comprise an angiogenic material at either or both of its end regions and/or along its length. In some embodiments, the method can facilitate the biointegration of an intraocular implant, such as an intraocular shunt, tube, pump, filter, or other fluid conductor with one or more body lumens or organ systems, and improve the healing of affected vasculature. For example, some embodiments relate to creating an artificial channel to permit aqueous flow from the anterior chamber to a venous structure in the eye to treat glaucoma. Some embodiments also relate to methods of creating artificial flow pathways and/or repairing flow pathways in the vascular system, including applications related to the heart or a vessel of the heart, an artificial kidney, the cerebral vascular system, and the venous and/or lymphatic vasculature. Some embodiments can facilitate the use of a medical device and improve its biointegration and connection to venous structures and/or lymphatic channels with which the medical device fluidly communicates.

For example, FIGS. 1-8B illustrate an eye and the use of an intraocular implant (shown as a shunt) being coupled to a venous vessel of the eye, such as an anterior ciliary vein. However, methods disclosed herein can also be used for other organ systems as well. For example, the methods disclosed herein can be used to fluidly interconnect a device with the vasculature, such as interconnecting an artificial kidney with the vasculature of a patient, treating a heart condition, relieving hydrocephalous, or treating cerebral ischemia.

Intraocular Implants and Methods

One common medical use for implants or shunts is in the treatment of glaucoma. Glaucoma is an eye condition in which the hydrostatic pressure within the eye is abnormally high, thereby resulting in damage to the optic nerve. The increased hydrostatic pressure can occur when there is insufficient outflow of aqueous humor fluid from the anterior chamber of the eye.

In a healthy eye, outflow or drainage occurs through two pathways—the conventional or trabecular pathway and the nonconventional or uveoscleral pathway. The conventional pathway consists of aqueous humor passing through the trabecular meshwork, across the inner wall of Schlemm's canal, into its lumen, and into draining collector channels, aqueous veins, and episcleral veins. The nonconventional route includes the uveal meshwork and anterior face of the ciliary muscle wherein the aqueous humor enters the connective tissue between the muscle bundles, through the suprachoroidal space, and out through the sclera (Goel et al., 2010, The Open Ophthamol J, 4:52-59). For a variety of reasons not fully understood, a resistance to the outflow of the aqueous humor can develop, leading to increased pressure, the hallmark symptom of glaucoma.

There are many treatments for the glaucoma condition that involve lowering the intraocular pressure, either by means of medication or surgery. In view of the importance of the trabecular network in outflow, surgical procedures focus on manipulating the trabecular network.

For example, a trabeculoplasty is a laser surgical procedure which changes the structure of the trabecular network in subtle ways so that aqueous fluid is able to pass more easily. When this procedure is not successful, the patient may undergo a trabeculectomy in which the surgeon creates a passage in the sclera for draining excess eye fluid.

Another procedure used in patients who do not sufficiently benefit from medicinal therapies or the surgical therapies described above is implant surgery in which an intraocular implant or aqueous shunt is positioned on the outside of the eye under the conjunctiva and a small tube or filament (shunt) is carefully inserted into the front chamber of the eye, just in front of the iris. The fluid can then drain through the tube into the area around the back end of the implant. The fluid collects here and is reabsorbed. This method also suffers from complications such as excessive scarring around the external drainage portion of the device, thereby blocking reabsorption of fluid, or the small opening in the tube in the front of the eye maybe become clogged.

Provided herein are devices and methods for use of an intraocular implant to create and maintain enhanced outflow of aqueous humor from the anterior chamber to reduce ocular pressure and treat disorders such as glaucoma as needed.

Referring now to the figures, some embodiments of the devices and methods disclosed herein can be implemented in the eye, thus providing an effective treatment for glaucoma.

FIG. 1 illustrates a cross-sectional view of an eye 10. Thick collagenous tissue known as sclera 11 covers the entire eye 10 except that portion covered by the cornea 12. The cornea 12 is a thin transparent tissue that focuses and transmits light into the eye and the pupil 14 which is the circular hole in the center of the iris 13 (colored portion of the eye). The cornea 12 merges into the sclera 11 at a juncture referred to as the limbus 15. The conjunctiva 16 is a thin membrane that covers the sclera 11 and cornea 12. The ciliary epithelium begins internally in the eye and extends along the interior of the sclera 11 and becomes the choroid 17. The choroid 17 is a vascular layer of the eye underlying retina 18. The optic nerve 19 transmits visual information to the brain.

The anterior chamber 20 of the eye 10, which is hound anteriorly by the cornea 12 and posteriorly by the iris 13 and lens 26, is filled with aqueous humor. Aqueous humor is a transparent fluid that is secreted from the ciliary body epithelium in the posterior chamber of the eye. The natural flow of aqueous humor in the eye is into the anterior chamber 20 and out of the anterior chamber through the trabecular meshwork 21. It then passes through Schlemm's canal 22 to be collected in channels at the back of Schlemm's canal 22. These collector channels gather together and form episcleral veins, which carry the aqueous humor out into the venous system to be circulated into the bloodstream.

Intraocular pressure of the eye 10 is maintained by the intricate balance of secretion and outflow of the aqueous in the manner described above. Glaucoma is characterized by the excessive buildup of aqueous fluid in the anterior chamber 20 which produces an increase in intraocular pressure (fluids are relatively incompressible and pressure is directed equally to all areas of the eye). The optic nerve 19 can be sequentially destroyed by glaucoma.

Figure 2:
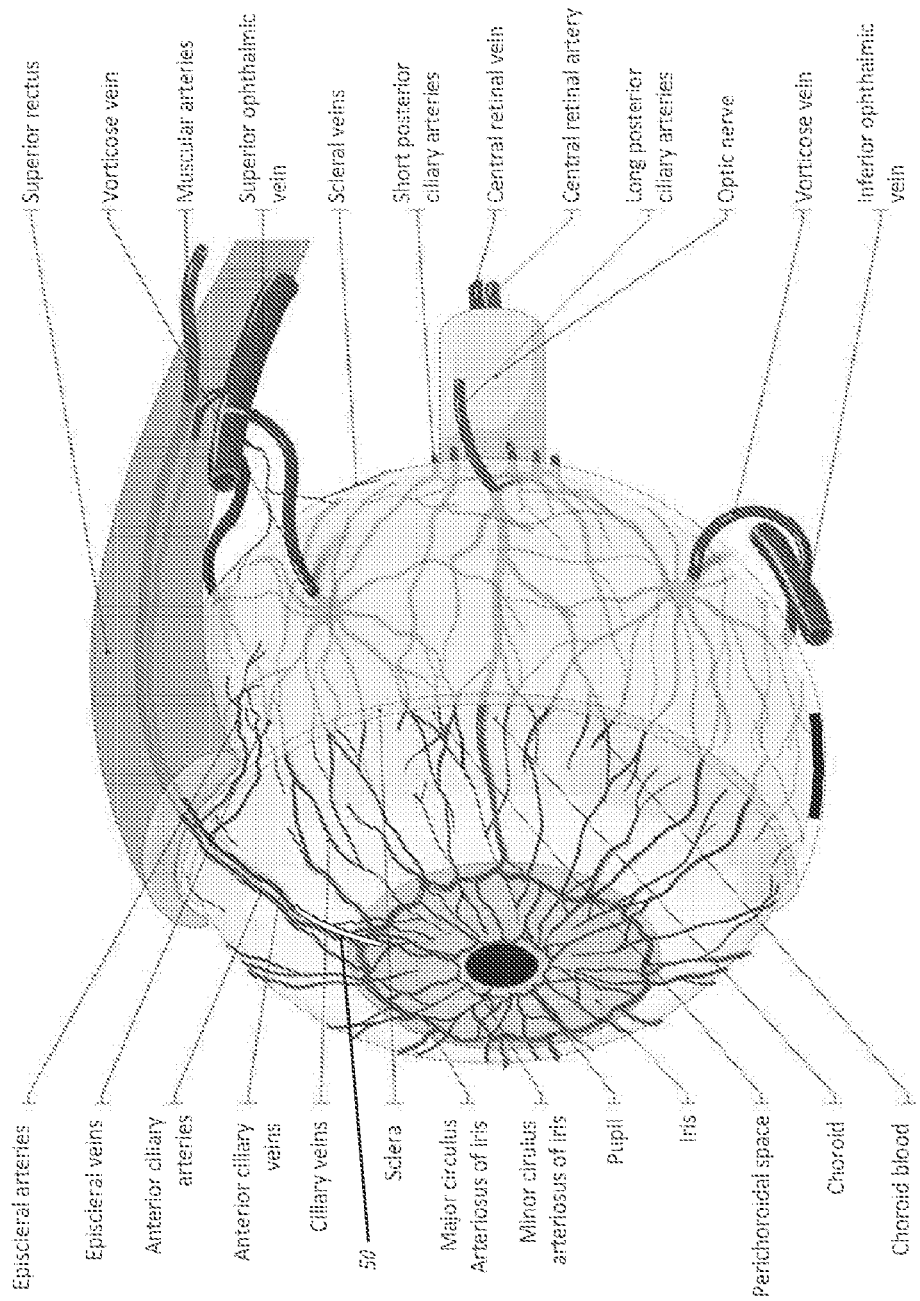
FIG. 2 is a perspective view of a diagrammatic representation of the vascular structure of the eye.
Figure 3:
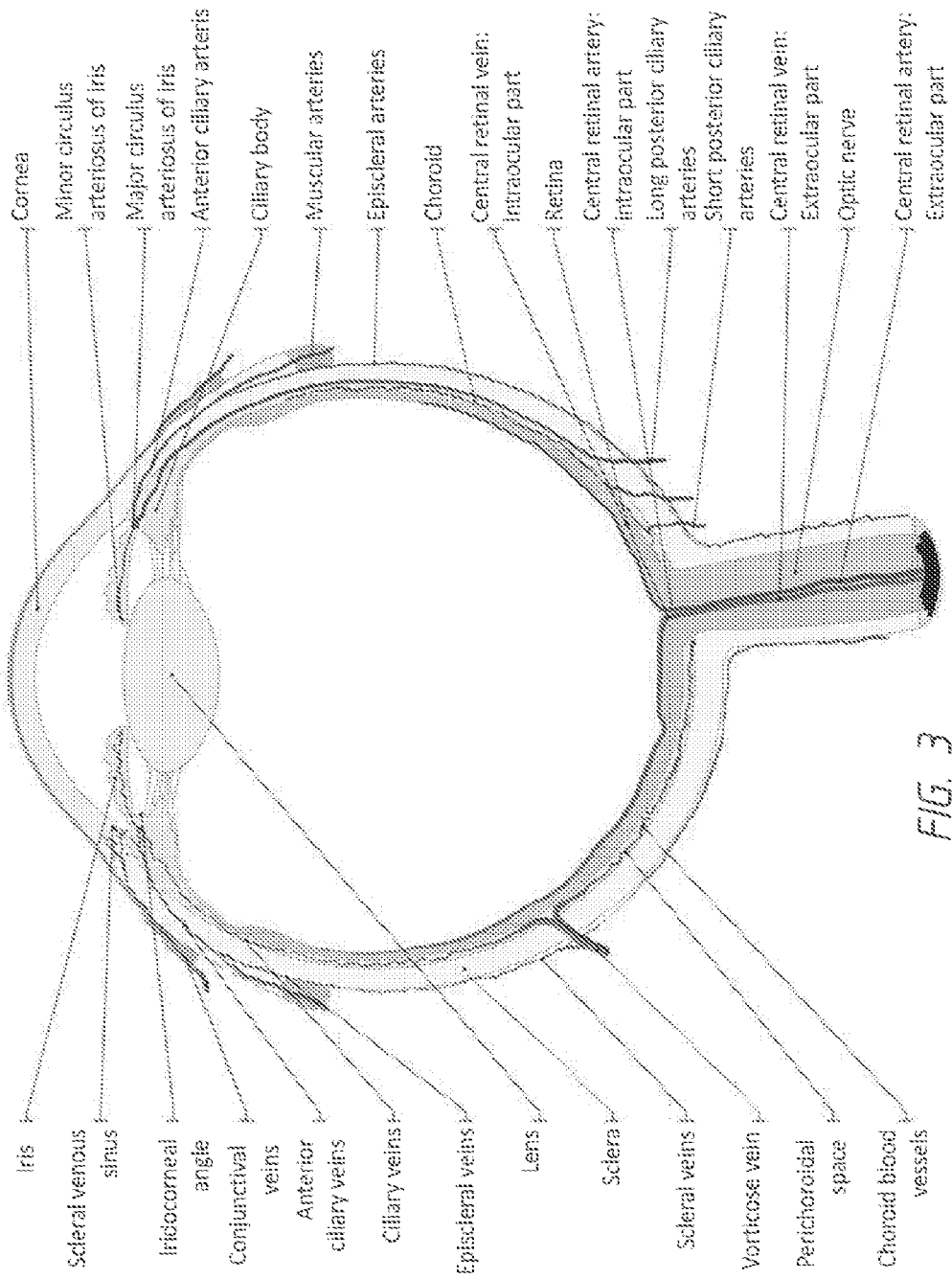
FIG. 3 is a cross-sectional view of the eye, illustrating the vascular structure thereof.
Figure 4:
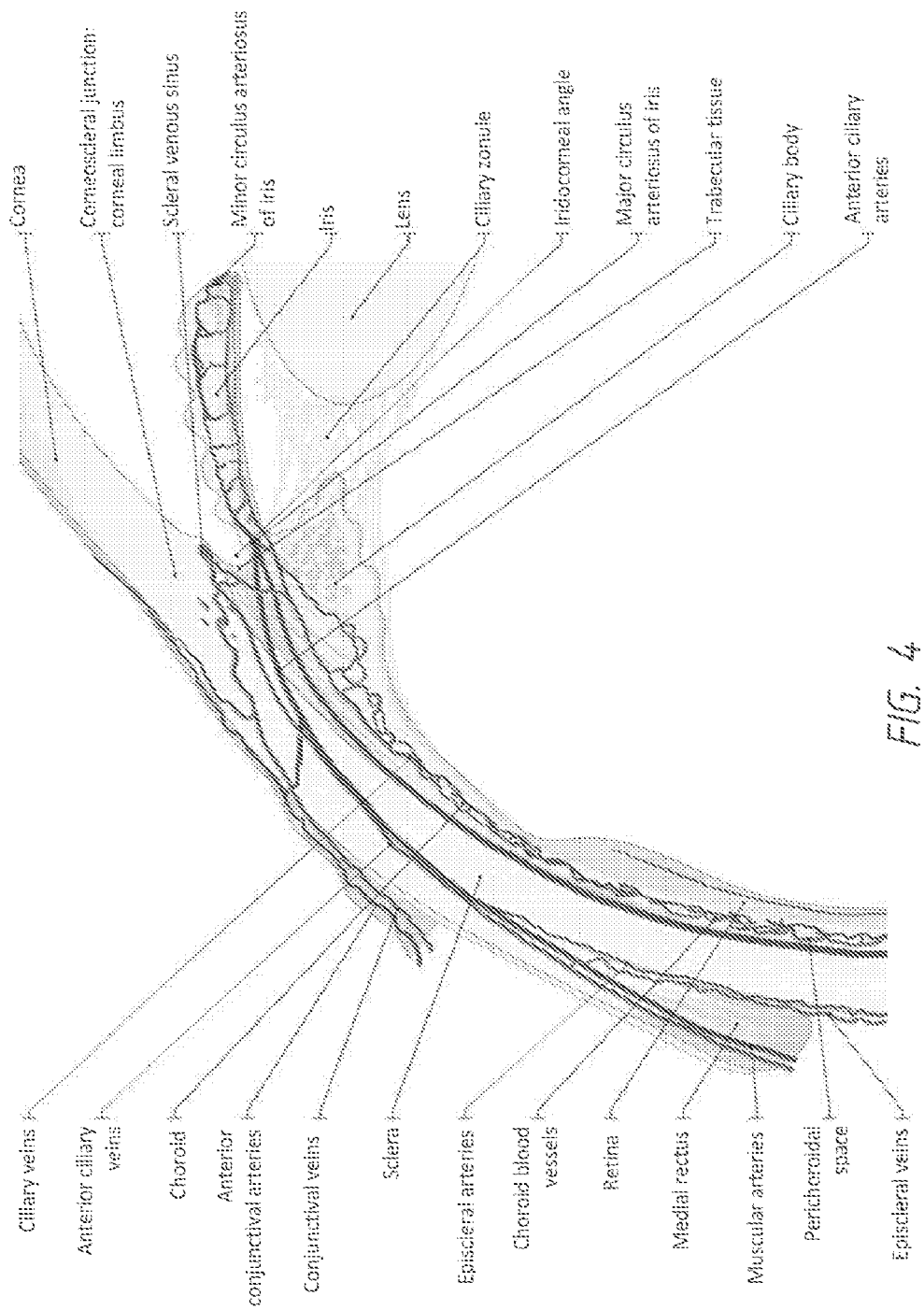
FIG. 4 is an enlarged cross-sectional view of the vascular structure of an anterior portion the eye.

As illustrated in FIGS. 2-4, the eye contains several small ciliary veins, anterior and posterior, that come from the ciliary body and empty into the superior and inferior ophthalmic veins. The anterior ciliary veins come from the ciliary body and normally carry blood only from the anterior ciliary muscle. As such, the anterior ciliary veins function primarily to transport blood and do not have a primary function of transporting aqueous humor from the anterior chamber. Further, anterior ciliary veins do not have the capacity to transport aqueous out of the eye at the rate necessary for the eye (e.g., at a rate approximately equal to the rate at which it is secreted from the ciliary epithelium). Thus, the anterior ciliary veins are not a natural outflow pathway for aqueous humor because they primarily function to transport blood, not aqueous humor. Indeed, transport of aqueous is naturally performed by the episcleral veins, which are distinct from anterior ciliary veins. The anterior ciliary venous system joins conjunctival and episcleral vessels at the limbus. Most of the venous drainage from the anterior segment is directed posteriorly into the choroid and thence into the vortex veins.

FIGS. 2-4 illustrate an extensive network of arteries and veins through which blood is supplied to the muscles and tissues of the eye. FIG. 2 illustrates aspects of the venous system of the eye, and FIGS. 3 and 4 illustrate cross-sectional views of the eye in which the venous and arterial systems are illustrated. Blood circulation through the eye generally occurs as follows. The ophthalmic artery supplies blood to various arteries in the eye. Some of these arteries include the anterior ciliary arteries, which pass into the sclera adjacent to the rectus muscle insertions. The anterior ciliary arteries meet to form the anterior episcleral arterial circle, which generally extends around the limbus and communicates with the major arterial circle of the iris. The eye also comprises anterior conjunctival veins and luminal arcades that drain blood into the limbal venous circle. In turn, the limbal venous circle drains blood into episcleral collecting veins that extend posteriorly through the sclera, emerging therefrom to form anterior ciliary veins. As shown in FIG. 4, the anterior ciliary veins extend from the ciliary body through the sclera, exit the sclera in an anterior section of the eye, and track along the rectus muscle.

Figure 5:
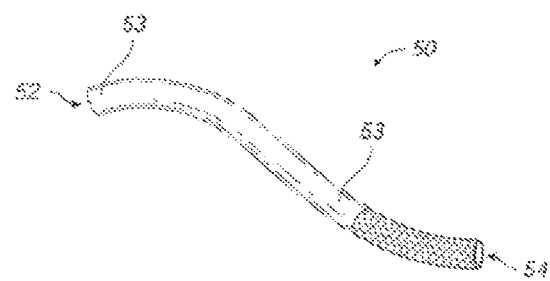
FIG. 5 illustrates an intraocular implant, according to some embodiments.
Figure 6:
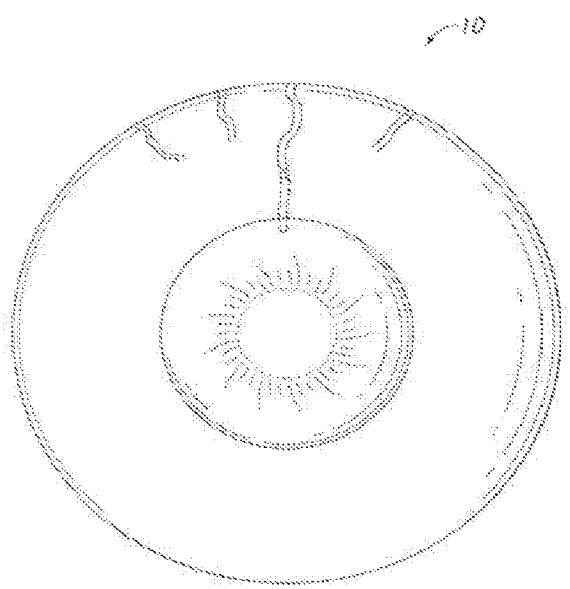
FIGS. 6-8B illustrate placements of an intraocular shunt in an eye, according to some embodiments.

Referring now to FIGS. 5 and 6, some embodiments can be provided in which an intraocular shunt is configured to fluidly interconnect the anterior chamber with a venous structure of the eye. The shunt can be positioned with an inflow end region positioned within the anterior chamber and an outflow end region adjacent to or cannulated within a vein, such as an anterior ciliary vein, or lymphatic channel in order to allow aqueous humor from the anterior chamber to drain into the vein or lymphatic channel, and can be aided by angiogenic factors (not using mechanical factors such as cannulation).

In accordance with some embodiments, the shunt can comprise an angiogenic material, such as a growth factor. Through angiogenesis, and angiogenic material can stimulate growth, healing, or repair of blood vessels. The angiogenic material can be carried on an outflow portion the shunt as a coating on the shunt and/or incorporated into the material of the shunt itself. For example, if an outflow end region of the shunt is positioned adjacent to a target venous structure, the angiogenic material can be used to stimulate blood vessel growth around the outflow end region in order to fluidly couple the outflow end region to the target venous structure. Further, in some embodiments, an outflow end region of the shunt can be positioned within a target venous structure, such as by cannulation of a vein, and the angiogenic material can be used to repair or heal the vein to ensure a viable coupling between the outflow end region and the target venous structure. Various aspects of angiogenic materials, such as a VEGF, are discussed further below and shown in FIGS. 9A-12B.

Referring again to FIG. 5, an intraocular shunt 50 can comprise an inflow region 52 that can be positioned in fluid communication with (e.g., extending into) the anterior chamber of the eye and a vascular connecting region 54 extending into a region of lower pressure of the eye. The shunt 50 can comprise a tubular or other shaped hollow member that can imbibe water. The shunt 50 can optionally comprise a porous material. The shunt 50 can be an aqueous transport member. For example, the shunt 50 can comprise a silicone material, a gelatin material, or other materials typical to vascular grafting materials.

The vascular connecting region 54 can be any suitable length or portion of the implant. In some embodiments, the vascular connecting region 54 can extend to reside in a supraciliary space, an intrascleral space, a suprachoroidal space, Schlemm's canal, or a subconjunctival space. The vascular connecting region can also extend adjacent to an episcleral vein or aqueous collector channels.

In some embodiments, the methods can perform using an ab interno or ab externo approach. Ab interno surgery involves piercing the cornea and advancing the shunt into the eye tissue, such as the anterior chamber angle or sclera, such that an inflow region of the shunt resides in a higher pressure chamber and an outflow region resides in a lower pressure chamber. In contrast, ab externo surgery involves piercing the eye tissue, such as sclera, and advancing the shunt through sclera and into fluid communication with the higher pressure chamber, such that an inflow region of the shunt resides in the higher pressure chamber and an outflow region resides in a lower pressure target area.

FIGS. 1 and 6 illustrate an embodiment of a shunt that has been inserted into the eye to provide fluid communication between the anterior chamber of the eye and one or more veins (shown as the anterior ciliary vein). The shunt can provide fluid communication between the anterior chamber and veins, such as one or more anterior ciliary veins, ciliary veins, conjunctival veins, and the scleral venous sinus.

FIGS. 7A-8B illustrate cross-sectional views of a target area of the eye adjacent to the ciliary body, posterior to the limbus. In some embodiments of the methods disclosed herein, a shunt 50 can be positioned within the eye such that an inflow region 52 is positioned within the anterior chamber 20 and a vascular connecting region 54 is positioned adjacent to one or more anterior ciliary veins or cannulated within an anterior ciliary vein. However, the anterior ciliary veins can be considered as an illustration of lymphatic channels for purposes of this disclosure. Such lymphatic channels can be found in the corneal limbus, the lacrimal gland, extraocular muscles, orbital meninges (dura matter of the optic nerve sheath), the ciliary body, and the choroid. Further, some lymphatic channels including the uveolymphatic pathway may also be accessed to provide a drainage channel.

Figure 7A:
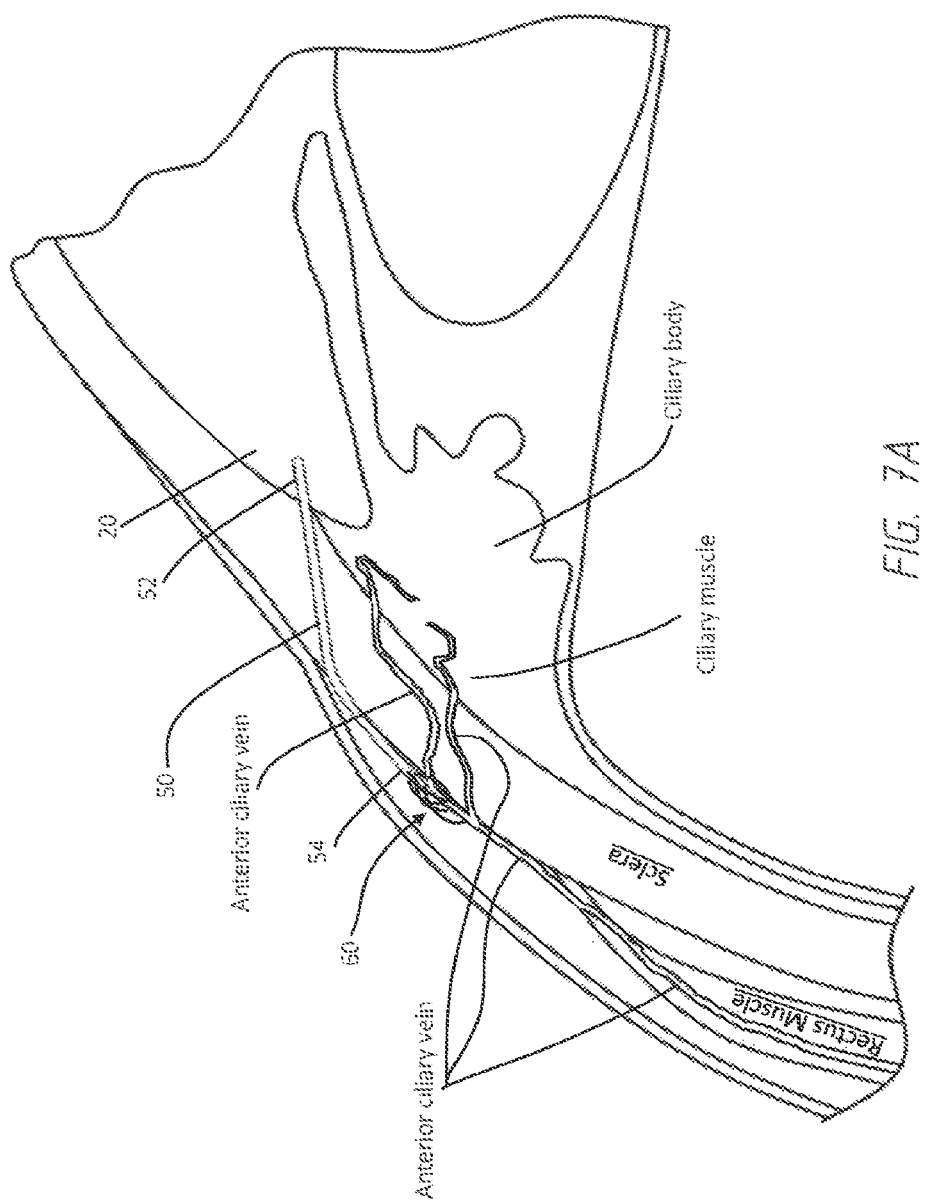
Figure 8A:
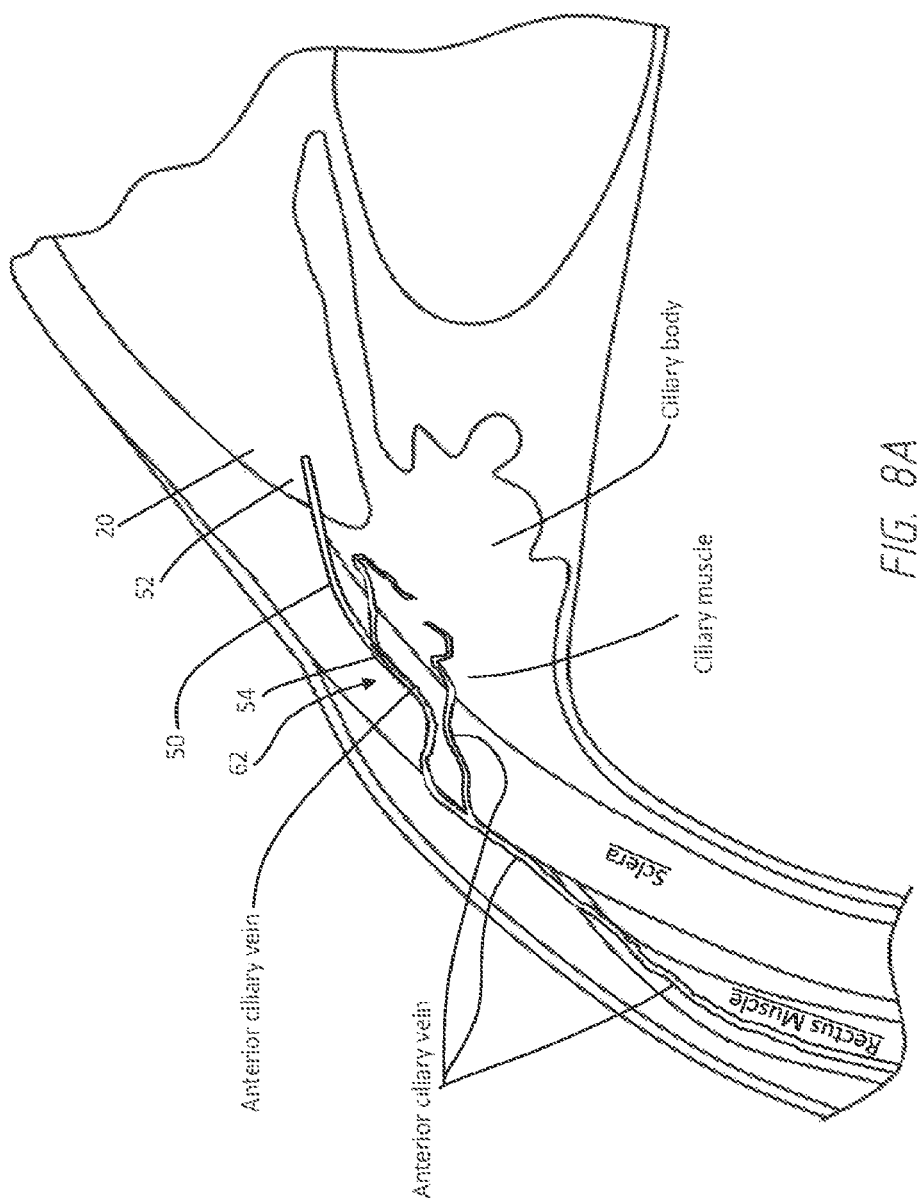

FIGS. 7A and 8A illustrate an embodiment in which the vascular connecting region 54 is positioned adjacent to an anterior ciliary vein. In such embodiments, the vascular connecting region 54 can comprise an angiogenic material that facilitates vessel growth to fluidly interconnect the shunt with the anterior ciliary vein. The growth of vessels 60 around and between the vascular connecting region 54 and the anterior ciliary vein can interconnect these structures to facilitate drainage of aqueous humor.

Figure 7B:
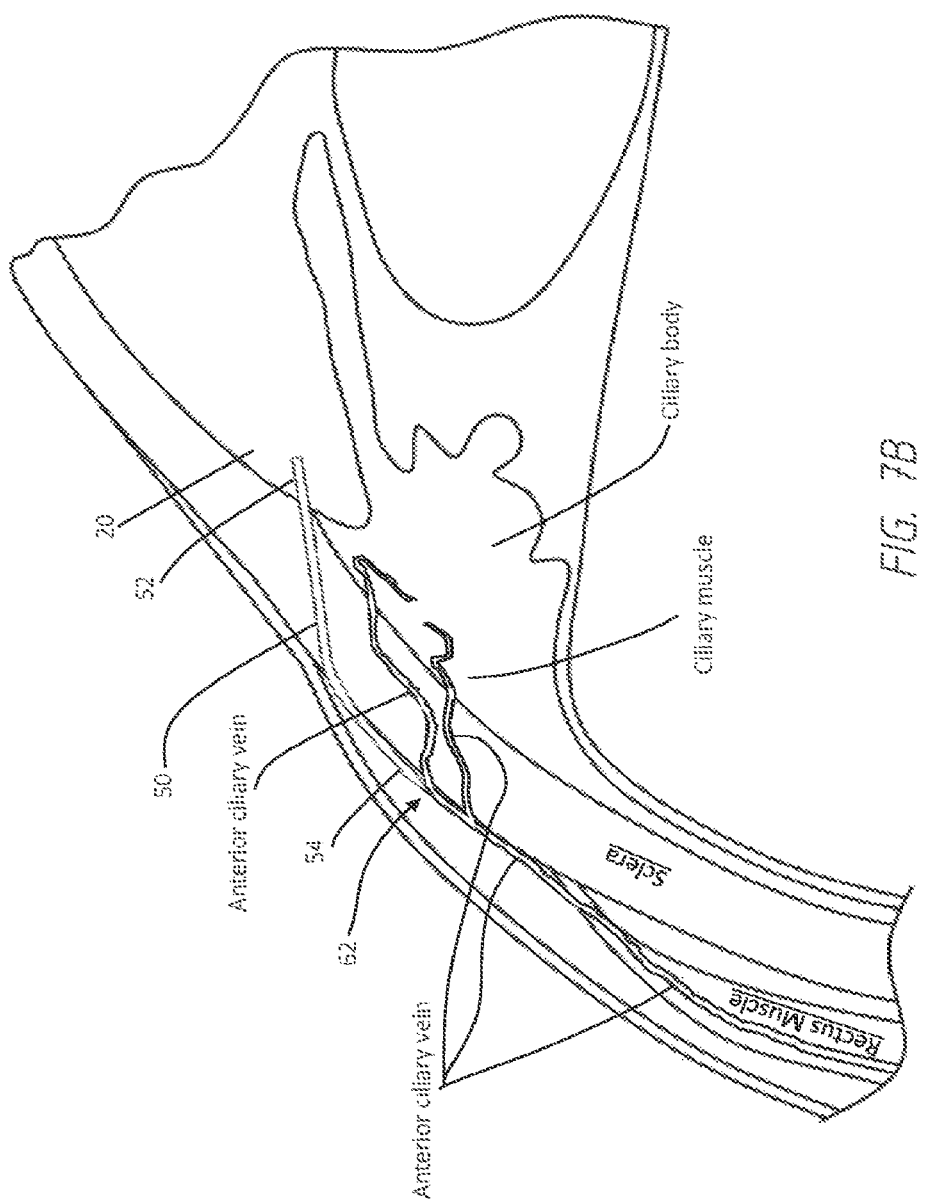
Figure 8B:
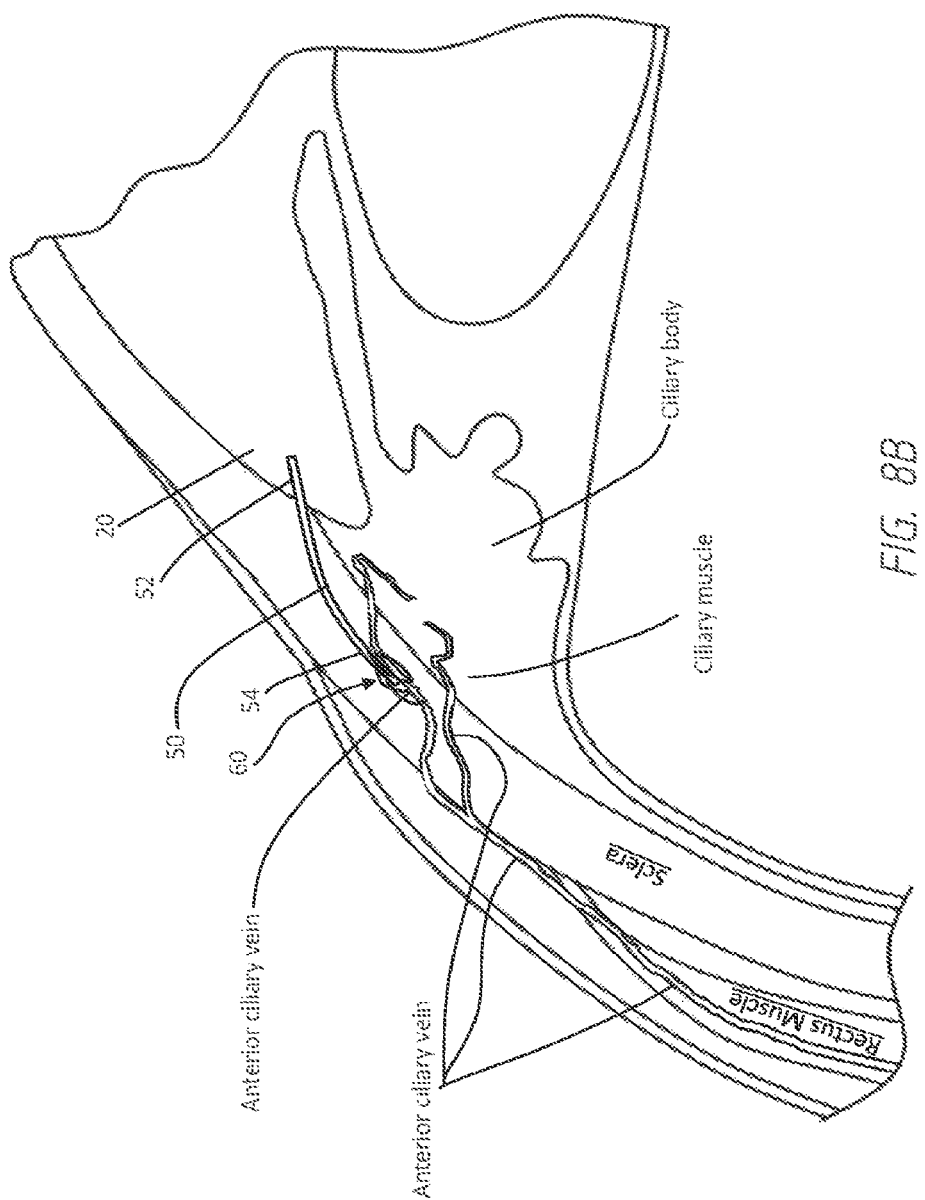

FIGS. 7B and 8B illustrate cross-sectional views the same target areas shown in FIGS. 7A and 8A. However, FIGS. 7B and 8B illustrate the vascular connecting region 54 being mechanically connected or cannulated 62 into the anterior ciliary vein to provide fluid communication between the shunt 50 and the anterior ciliary vein. In FIG. 7B, the vascular connecting region 54 of the shunt 50 is mechanically connected or cannulated 62 within the anterior ciliary vein at the anterior ciliary vein exit on the surface of the sclera. However, as shown in FIG. 8B, the vascular connecting region 54 of the shunt 50 can also be mechanically connected or cannulated within the anterior ciliary vein within the sclera.

Thus, in some embodiments, the vascular connecting region 54 can be positioned adjacent to the target outflow region and become fluidly interconnected with the venous structure or lymphatic through the creation of new vessels using an angiogenic material or growth factor. Further, in some embodiments, the vascular connecting region 54 can alternatively or additionally be cannulated or mechanically connected with the venous structure or lymphatic. The mechanical connection can be used in combination with an angiogenic material or growth factor in some embodiments.

In addition, some embodiments of the method can be implemented whereby the shunt extends from the anterior chamber to one of the rectus muscles. The shunt can be fluidly interconnected with the venous system within the rectus muscle. As with the methods noted above, when the vascular connecting region of the shunt is inserted into the rectus muscle, the vascular connecting region can include an angiogenic material or growth factor that facilitates vessel growth in order to fluidly interconnect the vascular connecting region of the shunt with the venous system of the rectus muscle. Alternatively, or in addition, the vascular connecting region can be mechanically coupled or cannulated into a venous structure (e.g., the anterior ciliary vein) within or superficial to the rectus muscle.

Accordingly, various outflow areas are provided herein that allow a shunt to fluidly interconnect with a lymphatic of the eye or the venous system of the eye, whether via intrascleral placement, suprascleral placement (e.g., at the anterior ciliary vein exit from the sclera), supra-rectus muscle placement, or intra-rectus muscle placement.

The suitability of a given vein as a target outflow area can be assessed by a surgeon, so that the delivery instrument (e.g., a shunt delivery tool or needle) can be placed an actuated in order to release the shunt into the eye, so that the vascular connecting region 54 achieves the desired target position. In some situations, it may be feasible to cannulate a vein, while in others, the vascular connecting region of the shunt may simply need to be positioned adjacent to the vein, so that angiogenic material of the shunt can encourage vessel growth to fluidly couple the vascular connecting region with the vein. Angiogenic material of a shunt used in a cannulation technique can be helpful to facilitate healing of the vein and biointegration of the shunt with the vein. This advantageous result may not occur when using prior mechanical cannulation techniques.

Further, the method can be performed using an ab interno or ab externo access method. The surgeon can advance a delivery instrument through the cornea, into the anterior chamber angle, and position a tip of the delivery instrument adjacent to the target venous structure. The shunt can be released therefrom such that the vascular connecting region remains positioned adjacent to the target venous structure (and in some embodiments, cannulated within a vein). In embodiments that employ a cannulation technique, the venous structure can be mechanically cannulated by mechanically puncturing the venous structure microscopically in a microsurgery and placing a portion of the vascular connecting region within the venous structure. In some embodiments, a surgeon can also tunnel either through the sclera or superficial to the sclera to the limbus, where the cornea meets the sclera, in order to position a shunt at the target venous structure.

When implanting a shunt, the surgeon should visualize the spatial relationship between the target vein and the vascular connecting region of the shunt. This can be performed using a gonio lens, or other magnifying equipment. In some instances, the target vein (whether one or more targeted) may be more easily visualized when dilated or enlarged, whether naturally, or by use of a dilating medium. Thus, in accordance with some embodiments, in preparation for performing the method, a surgeon can administer an agent to facilitate dilation of the target vein(s).

As noted herein, the method can be performed to fluidly couple a shunt with an anterior ciliary vein, veins in the episcleral area, veins in the Tenon's capsule, veins in the conjunctiva, or any vascular or venous structure in the anterior segment of the eye. Of the venous structure, the anterior ciliary vein can often be rather large, making these veins an excellent candidate target for the procedure. The anterior ciliary vein is also under the eye lid, so the eyelid will not erode a shunt positioned thereat. Arterial structures of the eye may be less desirable because the fluid pressure in such structures may be too high relative to the anterior chamber, thus restricting flow from the anterior chamber into the arterial structure. However, some embodiments disclosed herein can be used to fluidly interconnect a medical device with arterial structure(s), venous, and/or lymphatic structure(s) of the body.

The vascular connecting region 54 can comprise a growth factor, such as one or more of those listed herein. In some embodiments, the growth factor can be disposed or coated on the vascular connecting region 54. In other embodiments, the vascular connecting region 54 can comprise a resorbable material (as discussed further below) and the growth factor can be incorporated or impregnated into the resorbable material. After implantation of the shunt, the growth factor can begin to initiate or stimulate growth of new blood vessels 60. The new blood vessels 60 can provide an enhanced outflow pathway for aqueous humor draining from the anterior chamber.

Angiogenic and Therapeutic Materials

As noted above, in accordance with some embodiments, the shunt can comprise an angiogenic material, such as a growth factor, and/or one or more other therapeutic agents, such as those listed in U.S. patent application Ser. No. 14/848,030, filed on Sep. 8, 2015, or U.S. Pat. No. 7,708,711, the entireties of which are incorporated herein by reference. Through angiogenesis, and angiogenic material can stimulate the growth of or repair blood vessels. The angiogenic material can be carried by the implant, such as on an outflow portion or shunt, as a coating on the shunt and/or incorporated into the material of the implant. In accordance with some embodiments, the growth factor can stimulate growth of blood vessels and/or aqueous collector channels. For example, as illustrated in FIGS. 2-4, 7A, and 8A, an implanted shunt 50 having a growth factor disposed thereon can stimulate growth of new blood vessels.

FIG. 3 illustrates that, in some embodiments, the shunt 50 can comprise a vascular connecting region 54. The vascular connecting region 54 can comprise the growth factor. The growth factor can be coated onto or impregnated into the vascular connecting region 54.

The vascular connecting region 54 can extend along an outlet end region of the shunt. The vascular connecting region 54 can comprise any portion of the shunt, such as about one-half, one-third, one-fourth, one-fifth, one-sixth, one-seventh, or less of the overall shunt length. The shunt 50 can be configured as disclosed in co-pending U.S. patent application Ser. No. 14/848,030, filed on Sep. 8, 2015, the entirety of which is incorporated herein by reference.

In some embodiments, the growth factor can comprise a vascular endothelial growth factor (VEGF). VEGF is a sub-family of growth factors, and specifically, the platelet-derived growth factor family of cystine-knot growth factors. VEGF is an important signaling proteins involved in both vasculogenesis (the de novo formation of the embryonic circulatory system) and angiogenesis (the growth of blood vessels from pre-existing vasculature).

VEGF can be produced by certain organs to restore the oxygen supply to tissues when blood circulation is inadequate. For example, VEGF's normal function is to create new blood vessels during embryonic development, new blood vessels after injury, muscle following exercise, and new vessels (collateral circulation) to bypass blocked vessels.

For example, included within the family of VEGF, VEGF-A can facilitate angiogenesis, including the migration of endothelial cells, mitosis of endothelial cells, methane monooxygenase activity, αvβ3 activity, creation of blood vessel lumens, creation of fenestrations, chemotactic for macrophages and granulocytes, and vasodilation (indirectly by NO release). Further, VEGF-B can facilitate embryonic angiogenesis (e.g., in myocardial tissue). VEGF-C can facilitate lymphangiogenesis. VEGF-D can facilitate the development of lymphatic vasculature surrounding lung bronchioles. Further, PlGF can facilitate vasculogenesis and be used for angiogenesis during ischemia, inflammation, wound healing, and cancer.

Further, the broad term VEGF covers a number of proteins from two families, that result from alternate splicing of mRNA from a single, 8-exon, VEGF gene. The two different families are referred to according to their terminal exon (exon 8) splice site—the proximal splice site (denoted VEGFxxx) or distal splice site (VEGFxxxb). In addition, alternate splicing of exon 6 and 7 alters their heparin-binding affinity, and amino acid number (in humans: VEGF121, VEGF121b, VEGF145, VEGF165, VEGF165b, VEGF189, VEGF206; the rodent orthologs of these proteins contain one fewer amino acid). These domains have important functional consequences for the VEGF splice variants, as the terminal (exon 8) splice site determines whether the proteins are pro-angiogenic (proximal splice site, expressed during angiogenesis) or anti-angiogenic (distal splice site, expressed in normal tissues). In addition, inclusion or exclusion of exons 6 and 7 mediate interactions with heparan sulfate protcoglycans (HSPGs) and neuropilin co-receptors on the cell surface, enhancing their ability to bind and activate the VEGF receptors (VEGFRs). Recently, VEGF-C has been shown to be an important inducer of neurogenesis in the murine subventricular zone, without exerting angiogenic effects.

However, VEGF can contribute to disease when it is overexpressed. For example, solid cancers cannot grow beyond a limited size without an adequate blood supply; cancers that can express VEGF are able to grow and metastasize. Further, overexpression of VEGF can contribute to macular degeneration, such as age-related macular degeneration (AMD) and vascular disease in the retina of the eye and other parts of the body.

Accordingly, although growth factors are known, the prior art does not teach the use of growth factors in the eye. Instead, the prior art teaches the use of drugs, such as anti-VEGF, in the eye to impede growth of blood vessels.

Anti-VEGF therapies are important to stop new blood vessel growth in cancers and in other eye diseases, such as diabetic retinopathy or macular degeneration. Such therapies can use drugs such as Ranibizumab (Lucentis™), Bevacizumab (Avastin®), lapatinib (Tykerb), sunitinib (Sutent), sorafenib (Nexavar), axitinib, pazopanib, THC, and Cannabidiol, can inhibit VEGF and control or slow cancers or diseases such as AMD. For example, Lucentis™ is an antibody fragment that can be injected into the eye to bind to a VEGF, inactivate a VEGF, and stop new blood vessel growth. The use of products such as Lucentis™ allows a clinician to mitigate or prevent metastasizing of cancer cells. Accordingly, current therapies for macular degeneration, for example, therefore relies on anti-VEGF therapy.

Therefore, in the context of eye diseases, VEGF has been considered undesirable and therapy using growth factors such as a VEGF would not be considered desirable or obvious to a person of skill. As noted above, the body's own development of a VEGF in the eye occurs with disease, such as diabetic retinopathy and macular degeneration. In these diseases, the body forms new blood vessels on the retina. These blood vessels are bad because they can bleed, leak fluid, and cause sub-retinal fluid collections, retinal detachment, hemorrhaging, and blindness, especially when it is on the macula. Accordingly, a clinician would attempt to stop blood vessel growth by administering drugs such as Lucentis™.

Additionally, VEGF can be used to overcome harmful conditions of the heart, such as to connect blood vessels with blood vessels in situations where a coronary heart vessel has been blocked by plaque. For example, a VEGF is naturally produced by the heart over time to develop collateral vessels that mitigate vessel blockages. These collaterals are created very slowly over the course of a person's lifetime. However, although this function and use of a VEGF may be encouraging, Applicant recognizes that this use is exclusively limited to connecting new blood vessels with existing blood vessels. However, there are no methods or apparatuses known in the art that facilitate connection between new blood vessels and artificial fluid conduits, such as non-blood fluid conduits.

Accordingly, some embodiments disclosed herein provide novel methods and systems for developing flow pathways using a growth factor to relieve intraocular pressure. As noted, the methods and apparatuses disclosed herein can use a growth factor, such as a VEGF. Some embodiments can use a protein, such as a VEGF, which can be impregnated or encoded with a gene. For example, a VEGF is a class of a protein that is encoded by a gene. Various types of a VEGF can be formulated and used in some embodiments.

A listing of growth factor protein families from which one or more growth factors can be used in accordance with some embodiments, include: Adrenomedullin (AM); Angiopoietin (Ang); Autocrine motility factor; Bone morphogenetic proteins (BMPs); Brain-derived neurotrophic factor (BDNF); Epidermal growth factor (EGF); Erythropoietin (EPO); Fibroblast growth factor (FGF); Glial cell line-derived neurotrophic factor (GDNF); Granulocyte colony-stimulating factor (G-CSF); Granulocyte macrophage colony-stimulating factor (GM-CSF); Growth differentiation factor-9 (GDF9); Hepatocyte growth factor (HGF); Hepatoma-derived growth factor (HDGF); Insulin-like growth factor (IGF); Migration-stimulating factor; Myostatin (GDF-8); Nerve growth factor (NGF) and other neurotrophins; Platelet-derived growth factor (PDGF); Thrombopoietin (TPO); Transforming growth factor alpha (TGF-α); Transforming growth factor beta (TGF-β); Tumor_necrosis_factor-alpha (TNF-α); Vascular endothelial growth factor (VEGF); Wnt Signaling Pathway; placental growth factor (PlGF); [(Foetal Bovine Somatotrophin)] (FBS); IL-1 Cofactor for IL-3 and IL-6 (activates T cells); TL-2 T-cell growth factor (stimulates IL-1 synthesis and activates B-cells and NK cells); IL-3 (stimulates production of all non-lymphoid cells); IL-4 (growth factor for activated B cells, resting T cells, and mast cells); IL-5 (induces differentiation of activated B cells and eosinophils); IL-6 (stimulates Ig synthesis and growth factor for plasma cells); IL-7 (growth factor for pre-B cells), as well as other known or developed growth factors. VEGF-related proteins can include: VEGF-A, VEGF-B, VEGF-C, VEGF-D, VEGF isoforms, or other related proteins.

Some embodiments provide that a sequence identity to a gene or protein can be at least about 80%. For example, the sequence identity can be at least about 90%. Further, in some embodiments, the sequence identity can be at least about 95%. The sequence can be of base pairs if it is a gene or DNA, or the sequence can be amino acids if it is a protein. Some embodiments can use VEGF, the protein. Sequence identities for VEGF-A, VEGF-B, VEGF-C, and VEGF-D are illustrated in FIGS. 9A-12B.

Resorbable Materials

As noted above, in some embodiments, the vascular connecting region of the shunt can comprise a resorbable portion. In some embodiments, the vascular connecting region 54 can be entirely resorbable.

Additionally, the resorbable portion can extend across any length or amount of the vascular connecting region or shunt length. The resorbable portion of the shunt 100, 150 can comprise from about 1/10 to about 1/2 of the length of the shunt. In some embodiments, the resorbable portion can comprise 1/8 to about 1/3 of the length of the shunt. Additionally, the resorbable portion can comprise about 1/6 to about 1/4 of the length of the shunt. For example, the resorbable portion can comprise about 1/5 to about 1/3 of the length of the shunt.

In some embodiments, the vascular connecting region of the shunt can be only partially resorbable. For example, the shunt can have at least some non-resorbable material extending over its entire length. In some embodiments, the vascular connecting region can be formed from a non-resorbable polymeric material having a series of apertures or recesses that accommodate a resorbable material, as illustrated in co-pending U.S. patent application Ser. No. 14/848,030, filed on Sep. 8, 2015, the entirety of which is incorporated herein by reference.

Further, in some embodiments, the resorbable portion can comprise an angiogenic material or growth factor, such as a VEGF or other growth factor that is configured to facilitate growth of blood vessels. For example, the resorbable portion can be impregnated with a growth factor, such as a VEGF, and in use, the resorbable material can be dissolved into body tissue and release the growth factor. However, the growth factor can also or alternatively be carried in a coating disposed on the non-resorbable material and/or the resorbable material such that new blood vessel growth is promoted as the coating dissolves.

In accordance with some embodiments, the resorbable material can dissolve into a region of the eye within a range of from about two weeks to about 12 weeks. Further, the resorbable material can dissolve within a range of from about four weeks to about 10 weeks. Furthermore, the resorbable material can dissolve within a range of from about six weeks to about eight weeks.

FDA-approved resorbable materials include poly L-lactic acid (PLLA), poly(lactic-co-glycolic acid) (PLGA), polyethylene glycol (PEG), polyglycolic acid (PGA), and poly-ε-caprolactone (PCL). Accordingly, the resorbable material for use in the present devices can be comprised of any of the above. In addition, the resorbable material may be fabricated to incorporate angiogenic material. Examples of angiogenic materials include growth factors. In an exemplary embodiment, the growth factor is vascular endothelial growth factor (VEGF). The VEGF can comprise the sequence of any one of SEQ ID NOS:1-17, for example.

As described herein, the resorbable material is one that can be infused with the angiogenic material to allow controlled release over time of the angiogenic material and to also provide an environment in which the angiogenic material remains stable and functional by the time of its release from the vascular connecting region 54. Angiogenic factors useful for the presently described devices and methods include VEGF and various other protein molecules which can facilitate tissue restructuring and create artificial flow pathways and/or repair flow pathways in the eye. Use of functional proteins requires a scaffold composition which allows imbibed protein molecules to maintain their native structure over time prior to release from the implant.

Recently, new forms of resorbable scaffolds have been developed which have shown to be useful for the extended delivery of functional proteins such as VEGF. These scaffold materials are useful for the delivery devices described herein, especially the vascular connecting region 54. For example, Marchioli et al. (2016, Adv. Healthcare Mater., 5:1606-1616) describes a polycaprolactone (PCL) scaffold with a heparinized surface to electrostatically bind VEGF. Specifically, a macroporous PCL scaffold is fabricated by 3D fiber deposition and heparin is covalently bound to the polymer using 1-ethyl-3-(3-dimethylaminopropyl)carbodiimide/N-hydroxy succinimide (EDC-NHS) chemistry and the scaffold is functionalized with electrostatically bound protein. Synthesis of the PCL scaffold with heparinized surface can be done according to the methods of Marchioli et al. (2016, Adv. Healthcare Mater., 5:1606-1616). In some embodiments, the scaffold is functionalized with electrostatically bound VEGF-A (SEQ ID NO:1) or an isoform or variant thereof, including but not limited to any one of SEQ ID NOS:2-17.

In some embodiments, the vascular connecting region 54 is comprised of, encased by, or coated by a scaffold mesh composed of PCL-collagen blend (PCL/Col) fibers intermixed with deposits of hyaluronic acid hydrogel wherein the mesh is loaded with VEGF-A (SEQ ID NO:1) or an isoform or variant thereof, including but not limited to any one of SEQ ID NOS:2-17 (see, e.g., Ekaputra et al., 2011, Biomaterials, 32:8108-8117; Ekaputra et al, 2008, Biomacromolecules, 9:2097-2103)). Using the methods of Ekaputra et al. (2008 and 2011), PCL/Col-Hep scaffolds are fabricated in which an angiogenic material is loaded into the hydrogel mix. In some embodiments, the PCL/Col-Hep scaffold contains a ratio of about 4:1 PCL:Col.

An alternative embodiment for construction of the vascular connecting region 54 is use of a polyester, poly-(hydroxymethylglycolide-co-ε-caprolactone) (pHMGCL) (see, e.g., Seyednejad et al., 2012, Biomacromol, 13:3650-3660). The pHMGCL is fabricated with PCL and with a functional protein in the presence of bovine serum albumin (BSA) as a stabilizing agent. A resorbable material is made using pHMGCL/PCL solutions to prepare a fiber shell. The release of the angiogenic protein by the fabricated material can be modulated by, for example, varying the ratio of PCL and pHMGCL in the composition. The ratio of PCL:pHMGCL can be range from 1:1 to 1:2. The PCL/pHMGCL can be fabricated to comprise the stabilizing protein and angiogenic factor according to the methods of Seyednejad et al. (2012, Biomacromol, 13:3650-3660). In particular, the pHMGCL is prepared with a stabilizing protein and VEGF-A (SEQ ID NO:1) or an isoform or variant thereof, including but not limited to any one of SEQ ID NOS:2-17 and used to fabricate the vascular connecting region 54. In some embodiments, the stabilizing protein is BSA.

Fabrication of the shunt using any of the resorbable scaffolds described above infused with an angiogenic protein such as VEGF or variant or isoform thereof is done according to methods described in the art, for example, as referenced above. The resorbable scaffold compositions can be fabricated with varying amounts of the functional protein and made to release the protein at varying rates and over varying periods of time. In some embodiments, the angiogenic protein is released over a period of 1 to 6 weeks, 1 to 5 weeks, 1 to 4 weeks, 1 to 3 weeks, 1 to 2 weeks, 1 to 7 days, 1 to 5 days or 1 to 3 days.

Pump Mechanisms

In accordance with some embodiments, the shunt can comprise a pump mechanism. The pump mechanism can be configured to draw fluid from the anterior chamber toward another location of the eye. In some embodiments, the pump mechanism can be used in combination with the growth factor, which can allow the pump mechanism to draw fluid from the anterior chamber toward existing veins and/or newly formed or growing episcleral veins. Pump-type implants can be implanted into the eye using either the ab interno or the ab externo placement procedure. Pump mechanisms can therefore be incorporated into some embodiments disclosed herein, such as those disclosed in co-pending U.S. patent application Ser. No. 14/848,030, filed on Sep. 8, 2015, the entirety of which is incorporated herein by reference.

Alternative Treatments

The apparatus and methods discussed herein are not limited to the delivery and use of a medical device within the eye, but may include any number of further treatment applications. Other treatment sites may include areas or regions of the body, including any hollow anatomical structures. For example, the apparatus and methods discussed herein can be used for cerebral implants, coronary, implants, and kidney implants, to name a few.

Cerebral Implants and Methods

In addition, some embodiments may provide methods for treating hydrocephalus or intracranial hypertension. Hydrocephalus is a condition in which excessive fluid accumulates in the skull and exerts pressure on the brain. The fluid is a cerebrospinal fluid (CSF), a clear fluid that surrounds the brain and spinal cord. The excessive accumulation of CSF causes an abnormal widening of spaces in the brain, which are called ventricles. Potentially harmful pressure on the tissues of the brain can result from the widening of the ventricles.

Accordingly, in some embodiments, a shunt having a growth factor can be placed such that an inflow end region is positioned in an area of fluid accumulation in the skull (such as any of the first through fourth ventricles or other areas of fluid accumulation) and an outflow end region is positioned distally and adjacent to local vasculature. Over time, the growth factor can stimulate vascular growth and permit the shunt to be in direct fluid communication with blood vessels, thereby alleviating intracranial pressure. Thus, the shunt can fluidly interconnect blood vessels with a non-blood artificial conduit to the ventricles.

Some embodiments can also be used to treat cerebral ischemia, which is a condition in which an insufficient amount of blood is supplied to the brain. This condition can be caused by disease, compression of blood vessels, artery blockage, defects, and a variety of other factors. In implementing methods to treat cerebral ischemia, a shunt can be placed to bypass the damaged or compromised artery. The shunt can comprise an angiogenic material at either or both of its end regions, to facilitate bio integration in connection of the shunt to the venous structures and/or lymphatic channels. Accordingly, the shunt can serve to restore or improve flow to the cerebral tissue.

Some embodiments of the shunt and/or methods described herein can incorporate one or more features of implants, methods, and/or shunt delivery systems disclosed in co-pending U.S. patent application Ser. No. 14/848,030, filed on Sep. 8, 2015, the entirety of which is incorporated herein by reference.

Coronary Implants and Methods

In accordance with some embodiments, the methods disclosed herein can be implemented in performing coronary artery bypass surgery, percutaneous coronary intervention, a femoropopliteal bypass (Fem-Pop bypass) for peripheral arterial disease, or other such procedures. For example, the shunt can be placed adjacent to another structure to interconnect or improve fluid communication between the structure and the vascular system. In some embodiments, the shunt can be placed at a bypass. The bypass can comprise a percutaneous bypass, a femoropopliteal bypass (Fem-Pop bypass) for peripheral arterial disease, or other structures.

Artificial Kidney Implants and Methods

Hemodialysis is a procedure through which a patient's blood is filtered much in the same way that a human kidney performs. The instrument used to perform this filtering is called an artificial kidney. While current research is continuing to develop additional options for treating patients that require artificial kidney, it is contemplated that some embodiments disclosed herein can facilitate implantation and integration of the artificial kidney with the body. For example, using a tubular structure having an angiogenic material at the inflow or outflow region thereof can improve the biocompatibility and fluid interconnection of the tubular structure (and artificial kidney coupled thereto) with the patient's vascular system.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A method of fluidly interconnecting an implant with a venous structure or lymphatic, the method comprising: inserting the implant into a body using a delivery device, the implant having first and second end regions; positioning the first end region in a target area; positioning the second end region adjacent to the venous structure or lymphatic; and withdrawing the delivery device from the body.

Clause 2. The method of Clause 1, wherein the venous structure comprises an anterior ciliary vein of an eye.

Clause 3. The method of Clause 1, wherein the second end region is positioned adjacent to a lymphatic of an eye.

Clause 4. The method of Clause 3, wherein the lymphatic is located at a corneal limbus, a lacrimal gland, an extraocular muscle, an orbital meninges, a ciliary body, a choroid, or a uveolymphatic pathway of the eye.

Clause 5. The method of any one of the preceding Clauses, wherein the second end region is positioned adjacent to a vein extending within an anterior segment of an eye.

Clause 6. The method of Clause 1, wherein the second end region is positioned adjacent to a vein extending within Tenon's capsule, conjunctiva, or sclera.

Clause 7. The method of any one of the preceding Clauses, wherein the positioning the second end region comprises positioning the second end region within a venous structure of an eye to cannulate the venous structure.

Clause 8. The method of Clause 7, wherein the positioning the second end region within the venous structure comprises puncturing the venous structure and inserting the second end region into the venous structure.

Clause 9. The method of Clause 8, wherein the positioning the second end region within the venous structure is performed using a microscope.

Clause 10. The method of Clause 1, wherein the venous structure comprises a heart or a vessel of the heart.

Clause 11. The method of Clause 1, wherein the venous structure comprises vessels of an artificial kidney.

Clause 12. The method of Clause 1, wherein the venous structure comprises a vein of a cerebral vascular venous system.

Clause 13. The method of any one of Clauses 1 to 9, wherein the positioning the first end region comprises positioning the first end region in an anterior chamber of an eye.

Clause 14. The method of any one of Clauses 1 to 9 and 13, wherein the positioning the second end region comprises positioning the second end region such that the second end region either (i) resides in a supraciliary space, an intrascleral space, a suprachoroidal space, Schlemm's canal, or a subconjunctival space, or (ii) adjacent to an episcleral vein or aqueous collector channels.

Clause 15. The method of any one of the preceding Clauses, wherein the second end region comprises a resorbable material and an angiogenic material.

Clause 16. The method of Clause 15, wherein the resorbable material comprises a macroporous polycaprolactone (PCL) scaffold with a heparinized surface to which an angiogenic material is bound.

Clause 17. The method of Clause 15, wherein the resorbable material comprises PCL-collagen blend fibers intermixed with hyaluronic acid hydrogel, wherein an angiogenic material is loaded into the fibers.

Clause 18. The method of Clause 15, wherein the resorbable material comprises polyester, poly-(hydroxymethylglycolide-co-ε-caprolactone) (pHMGCL), bovine serum albumin, and an angiogenic material.

Clause 19. The method of any one of the preceding Clauses, wherein the second end region comprises an angiogenic material.

Clause 20. The method of Clause 19, wherein the angiogenic material comprises a growth factor.

Clause 21. The method of Clause 20, wherein the growth factor comprises a vascular endothelial growth factor (VEGF).

Clause 22. The method of Clause 20, wherein the growth factor comprises a VEGF isoform.

Clause 23. The method of any one of Clauses 1 to 9 and 13 to 22, wherein the body comprises an eye, and the inserting an implant comprises an ab interno insertion into the eye through a cornea of the eye.

Clause 24. The method of any one of Clauses 1 to 9 and 13 to 22, wherein the body comprises an eye, and the inserting an implant comprises an ab externo insertion into the eye through sclera of the eye.

Clause 25. A method of deploying an intraocular implant into an eye for stimulating vascular growth, the method comprising: inserting into the eye a delivery device carrying the implant; releasing the implant from the delivery device such that an inflow region of the implant resides in a higher pressure chamber of the eye and a vascular connecting region of the implant resides adjacent to a venous structure or lymphatic of the eye, the implant having a lumen to conduct fluid therethrough to facilitate aqueous humor outflow from the higher pressure chamber to the venous structure or lymphatic; and withdrawing the delivery device from the eye.

Clause 26. The method of Clause 25, wherein the releasing comprises positioning the vascular connecting region within a vein of the eye to cannulate the vein.

Clause 27. The method of Clause 25 or 26, wherein the vein comprises an anterior ciliary vein.

Clause 28. The method of any one of Clauses 25 to 27, wherein the vascular connecting region of the implant comprises a growth factor for promoting growth of blood vessels adjacent to the venous structure or lymphatic to fluidly interconnect the venous structure or lymphatic to the implant.

Clause 29. The method of Clause 28, wherein the growth factor comprises a vascular growth factor selected from the group consisting of a VEGF isoform.

Clause 30. The method of Clause 28, wherein the growth factor comprises a VEGF.

Clause 31. The method of any one of Clauses 25 to 30, wherein the releasing the implant comprises positioning the vascular connecting region either (i) to reside in a supraciliary space, an intrascleral space, a suprachoroidal space, Schlemm's canal, or a subconjunctival space, or (ii) adjacent to an episcleral vein or aqueous collector channels.

Clause 32. The method of any one of Clauses 25 to 31, wherein the higher pressure chamber comprises an anterior chamber of the eye.

Clause 33. The method of any one of Clauses 25 to 32, wherein the implant comprises a growth factor coated onto the vascular connecting region.

Clause 34. The method of any one of Clauses 25 to 33, wherein the vascular connecting region comprises a resorbable material.

Clause 35. The method of any one of Clauses 25 to 33, wherein the vascular connecting region comprises a resorbable material and a growth factor.

Clause 36. The method of any one of Clauses 34 or 35, wherein the resorbable material comprises a macroporous polycaprolactone (PCL) scaffold with a heparinized surface to which the growth factor is bound.

Clause 37. The method of any one of Clauses 34 or 35, wherein the resorbable material comprises PCL-collagen blend fibers intermixed with hyaluronic acid hydrogel, wherein the growth factor is loaded into the fibers.

Clause 38. The method of Clause 34 or 35, wherein the resorbable material comprises polyester, poly-(hydroxymethylglycolide-co-ε-caprolactone) (pHMGCL), bovine serum albumin, and the growth factor.

Clause 39. The method of any one of Clause 35, 37 or 38, wherein the growth factor is impregnated into a resorbable material.

Clause 40. The method of Clause 25, wherein the vascular connecting region is positioned adjacent to a lymphatic of the eye.

Clause 41. The method of Clause 40, wherein the vascular connecting region is cannulated within a lymphatic of an eye.

Clause 42. The method of any one of Clauses 40 or 41, wherein the lymphatic is located at a corneal limbus, a lacrimal gland, an extraocular muscle, an orbital meninges, a ciliary body, a choroid, or a uvcolymphatic pathway of the eye.

Clause 43. An implant comprising any of the features or structures disclosed herein.

Clause 44. A method of placing an implant comprising: placing an implant having any of the features or structures disclosed herein into a body; and placing the implant to interconnect a venous structure or lymphatic of the body with a target outflow location.

Clause 45. The method of Clause 44, wherein the implant comprises an angiogenic material for promoting growth of new blood vessels in the target outflow location.

Further Considerations

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the inventions have been described, these have been presented by way of example only, and are not intended to limit the scope of the inventions. Indeed, the novel methods and systems described herein may be embodied in a variety of other forms without departing from the spirit thereof. The accompanying claims and their equivalents are intended to cover such forms or modifications as would fall within the scope and spirit of the inventions.

What is claimed is:

1. A method of fluidly interconnecting an implant with a venous structure or a lymphatic structure, the method comprising:
   inserting the implant into an eye using a delivery device, wherein the implant has a first inflow end region and an outflow end region;
   positioning the inflow end region in an anterior chamber of the eye;
   positioning the second outflow region in (i) a subconjunctival space or (ii) in or adjacent to an episcleral vein; and
   withdrawing the delivery device from the body;
   wherein the implant comprises an angiogenic material, and wherein the angiogenic material stimulates blood vessel growth around the outflow end region to fluidly couple the outflow end region to the venous structure or the lymphatic structure.

2. The method of claim 1, wherein the venous structure is an anterior ciliary vein of the eye.

3. The method of claim 1, wherein the outflow end region is positioned adjacent to (i) the lymphatic structure, (ii) a vein extending within an anterior segment of an eye, or (iii) a vein extending within Tenon's capsule, conjunctiva, or sclera.

4. The method of claim 3, wherein the lymphatic structure is located at a corneal limbus, a lacrimal gland, an extraocular muscle, an orbital meninges, a ciliary body, choroid, or a uveolymphatic pathway of the eye.

5. The method of claim 1, comprising positioning the outflow end region within the venous structure or the lymphatic structure to cannulate the venous structure or the lymphatic structure.

6. The method of claim 1, wherein the outflow end region comprises a scaffold comprising the angiogenic material.

7. The method of claim 6, wherein the scaffold composition comprises a resorbable material.

8. The method of claim 7, wherein the resorbable material comprises (i) a macroporous polycaprolactone (PCL) scaffold with a heparinized surface to which the angiogenic material is bound; (ii) PCL-collagen blend fibers intermixed with hyaluronic acid hydrogel, wherein the angiogenic material is loaded into the fibers; or (iii) polyester, poly-(hydroxymethylglycolide-co-e-caprolactone), bovine serum albumin, and the angiogenic material.

9. The method of claim 1, wherein the angiogenic material comprises a growth factor.

10. The method of claim 9, wherein the growth factor comprises a vascular endothelial growth factor (VEGF).

11. A method of deploying an intraocular implant into an eye for stimulating vascular growth, the method comprising:
   inserting into the eye a delivery device carrying the implant; releasing the implant from the delivery device such that an inflow region of the implant resides in a higher pressure chamber of the eye than a vascular connecting region of the implant, wherein the vascular connecting region of the implant resides in or adjacent to a venous structure or a lymphatic structure of the eye, the implant having a lumen to conduct fluid therethrough to facilitate aqueous humor outflow from the higher pressure chamber to the venous structure or the lymphatic structure; and
   withdrawing the delivery device from the eye;

wherein the implant comprises an angiogenic material, and wherein the angiogenic material promotes growth of blood vessels adjacent to the venous structure or the lymphatic structure to fluidly interconnect the venous structure or the lymphatic structure to the implant.

12. The method of claim 11, wherein the venous structure comprises an anterior ciliary vein.

13. The method of claim 11, wherein the angiogenic material comprises a growth factor.

14. The method of claim 13, wherein the growth factor comprises a VEGF.

15. The method of claim 11, wherein the higher pressure chamber is an anterior chamber of the eye.

16. The method of claim 11, wherein the angiogenic material is coated onto the vascular connecting region.

17. The method of claim 11, wherein the vascular connecting region comprises a scaffold composition comprising the angiogenic material.

18. The method of claim 17, wherein the scaffold composition comprises a resorbable material.

19. The method of claim 18, wherein the resorbable material comprises (i) a macroporous polycaprolactone (PCL) scaffold with a heparinized surface to which the angiogenic material is bound; (ii) a PCL-collagen blend fibers intermixed with hyaluronic acid hydrogel, wherein the angiogenic material is loaded into the fibers; or (iii) polyester, poly-(hydroxymethylglycolide-co-e-caprolactone), bovine serum albumin, and the angiogenic material.

20. The method of claim 11, wherein the vascular connecting region is cannulated within the lymphatic structure of the eye.

21. The method of claim 11, wherein the lymphatic structure is located at a corneal limbus, a lacrimal gland, an extraocular muscle, an orbital meninges, a ciliary body, choroid, or a uveolymphatic pathway of the eye.

* * * * *

SEQUENCE LISTING

```
<160> NUMBER OF SEQ ID NOS: 17

<210> SEQ ID NO 1
<211> LENGTH: 232
<212> TYPE: PRT
<213> ORGANISM: homo sapiens

<400> SEQUENCE: 1

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 2
```

-continued

<211> LENGTH: 215
<212> TYPE: PRT
<213> ORGANISM: homo sapiens

<400> SEQUENCE: 2

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Glu
            20                  25                  30

Gly Asp His Lys Pro His Glu Val Val Lys Phe Met Asp Val Tyr Arg
        35                  40                  45

Arg Ser Tyr Cys Arg Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Ala Gly Cys Cys Asn Asp Glu Ser Leu Glu Cys Val Pro
                85                  90                  95

Thr Glu Glu Phe Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Ala Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205

Arg Cys Asp Lys Pro Arg Arg
        210                 215
```

<210> SEQ ID NO 3
<211> LENGTH: 209
<212> TYPE: PRT
<213> ORGANISM: homo sapiens

<400> SEQUENCE: 3

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125
```

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Pro
145                 150                 155                 160

Cys Gly Pro Cys Ser Glu Arg Arg Lys His Leu Phe Val Gln Asp Pro
                165                 170                 175

Gln Thr Cys Lys Cys Ser Cys Lys Asn Thr Asp Ser Arg Cys Lys Ala
                180                 185                 190

Arg Gln Leu Glu Leu Asn Glu Arg Thr Cys Arg Cys Asp Lys Pro Arg
            195                 200                 205

Arg

<210> SEQ ID NO 4
<211> LENGTH: 191
<212> TYPE: PRT
<213> ORGANISM: homo sapiens

<400> SEQUENCE: 4

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 5
<211> LENGTH: 174
<212> TYPE: PRT
<213> ORGANISM: homo sapiens

<400> SEQUENCE: 5

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
                115                 120                 125

Glu Cys Arg Pro Lys Lys Asp Arg Ala Arg Gln Glu Asn Pro Cys Gly
130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Met
                165                 170

<210> SEQ ID NO 6
<211> LENGTH: 171
<212> TYPE: PRT
<213> ORGANISM: homo sapiens

<400> SEQUENCE: 6

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
                 20                  25                  30

Gly Gly Gln Asn His His Glu Val Val Lys Phe Met Asp Val Tyr Gln
                 35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
                115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Cys Asp Lys Pro Arg Arg
                165                 170

<210> SEQ ID NO 7
<211> LENGTH: 191
<212> TYPE: PRT
<213> ORGANISM: homo sapiens

<400> SEQUENCE: 7

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
                 20                  25                  30

-continued

Gly Gly Gln Asn His His Glu Val Lys Phe Met Asp Val Tyr Gln
         35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Ser Leu Thr Arg Lys Asp
            180                 185                 190

<210> SEQ ID NO 8
<211> LENGTH: 121
<212> TYPE: PRT
<213> ORGANISM: homo sapiens

<400> SEQUENCE: 8

Ala Pro Met Ala Glu Gly Gly Gln Asn His His Glu Val Val Lys
 1               5                  10                  15

Phe Met Asp Val Tyr Gln Arg Ser Tyr Cys His Pro Ile Glu Thr Leu
                 20                  25                  30

Val Asp Ile Phe Gln Glu Tyr Pro Asp Glu Ile Glu Tyr Ile Phe Lys
             35                  40                  45

Pro Ser Cys Val Pro Leu Met Arg Cys Gly Gly Cys Cys Asn Asp Glu
 50                  55                  60

Gly Leu Glu Cys Val Pro Thr Glu Glu Ser Asn Ile Thr Met Gln Ile
 65                  70                  75                  80

Met Arg Ile Lys Pro His Gln Gly Gln His Ile Gly Glu Met Ser Phe
                 85                  90                  95

Leu Gln His Asn Lys Cys Glu Cys Arg Pro Lys Lys Asp Arg Ala Arg
            100                 105                 110

Gln Glu Lys Cys Asp Lys Pro Arg Arg
        115                 120

<210> SEQ ID NO 9
<211> LENGTH: 137
<212> TYPE: PRT
<213> ORGANISM: homo sapiens

<400> SEQUENCE: 9

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
                 20                  25                  30

Gly Gly Gln Asn His His Glu Val Val Lys Phe Met Asp Val Tyr Gln
             35                  40                  45

-continued

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Cys Asp Lys Pro Arg Arg
        130                 135

<210> SEQ ID NO 10
<211> LENGTH: 371
<212> TYPE: PRT
<213> ORGANISM: homo sapiens

<400> SEQUENCE: 10

Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
                20                  25                  30

Gly Pro Glu Pro Ala Pro Gly Gly Val Glu Gly Val Gly Ala Arg
            35                  40                  45

Gly Val Ala Leu Lys Leu Phe Val Gln Leu Leu Gly Cys Ser Arg Phe
        50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
        130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

```
Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
                325                 330                 335

Asp Pro Gln Thr Cys Lys Cys Ser Cys Lys Asn Thr Asp Ser Arg Cys
            340                 345                 350

Lys Ala Arg Gln Leu Glu Leu Asn Glu Arg Thr Cys Arg Cys Asp Lys
        355                 360                 365

Pro Arg Arg
    370

<210> SEQ ID NO 11
<211> LENGTH: 327
<212> TYPE: PRT
<213> ORGANISM: homo sapiens

<400> SEQUENCE: 11

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Val Gly Val Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
```

```
            275                 280                 285
Ile Lys Pro His Gln Gly Gln His Ile Gly Glu Met Ser Phe Leu Gln
    290                 295                 300
His Asn Lys Cys Glu Cys Arg Pro Lys Lys Asp Arg Ala Arg Gln Glu
305                 310                 315                 320
Lys Cys Asp Lys Pro Arg Arg
                325

<210> SEQ ID NO 12
<211> LENGTH: 395
<212> TYPE: PRT
<213> ORGANISM: homo sapiens

<400> SEQUENCE: 12

Met Thr Asp Arg Gln Thr Asp Thr Ala Pro Ser Pro Ser Tyr His Leu
1               5                   10                  15
Leu Pro Gly Arg Arg Thr Val Asp Ala Ala Ser Arg Gly Gln
            20                  25                  30
Gly Pro Glu Pro Ala Pro Gly Gly Val Glu Gly Val Gly Ala Arg
            35                  40                  45
Gly Val Ala Leu Lys Leu Phe Val Gln Leu Leu Gly Cys Ser Arg Phe
    50                  55                  60
Gly Gly Ala Val Val Arg Ala Gly Glu Ala Glu Pro Ser Gly Ala Ala
65                  70                  75                  80
Arg Ser Ala Ser Ser Gly Arg Glu Glu Pro Gln Pro Glu Glu Gly Glu
                85                  90                  95
Glu Glu Glu Glu Lys Glu Glu Glu Arg Gly Pro Gln Trp Arg Leu Gly
                100                 105                 110
Ala Arg Lys Pro Gly Ser Trp Thr Gly Glu Ala Ala Val Cys Ala Asp
            115                 120                 125
Ser Ala Pro Ala Ala Arg Ala Pro Gln Ala Leu Ala Arg Ala Ser Gly
    130                 135                 140
Arg Gly Gly Arg Val Ala Arg Arg Gly Ala Glu Ser Gly Pro Pro
145                 150                 155                 160
His Ser Pro Ser Arg Arg Gly Ser Ala Ser Arg Ala Gly Pro Gly Arg
                165                 170                 175
Ala Ser Glu Thr Met Asn Phe Leu Leu Ser Trp Val His Trp Ser Leu
            180                 185                 190
Ala Leu Leu Leu Tyr Leu His His Ala Lys Trp Ser Gln Ala Ala Pro
    195                 200                 205
Met Ala Glu Gly Gly Gly Gln Asn His His Glu Val Val Lys Phe Met
    210                 215                 220
Asp Val Tyr Gln Arg Ser Tyr Cys His Pro Ile Glu Thr Leu Val Asp
225                 230                 235                 240
Ile Phe Gln Glu Tyr Pro Asp Glu Ile Glu Tyr Ile Phe Lys Pro Ser
                245                 250                 255
Cys Val Pro Leu Met Arg Cys Gly Gly Cys Cys Asn Asp Glu Gly Leu
                260                 265                 270
Glu Cys Val Pro Thr Glu Glu Ser Asn Ile Thr Met Gln Ile Met Arg
            275                 280                 285
Ile Lys Pro His Gln Gly Gln His Ile Gly Glu Met Ser Phe Leu Gln
    290                 295                 300
His Asn Lys Cys Glu Cys Arg Pro Lys Lys Asp Arg Ala Arg Gln Glu
305                 310                 315                 320
```

```
Lys Lys Ser Val Arg Gly Lys Gly Lys Gly Gln Lys Arg Lys Arg Lys
                325                 330                 335

Lys Ser Arg Tyr Lys Ser Trp Ser Val Pro Cys Gly Pro Cys Ser Glu
            340                 345                 350

Arg Arg Lys His Leu Phe Val Gln Asp Pro Gln Thr Cys Lys Cys Ser
        355                 360                 365

Cys Lys Asn Thr Asp Ser Arg Cys Lys Ala Arg Gln Leu Glu Leu Asn
370                 375                 380

Glu Arg Thr Cys Arg Cys Asp Lys Pro Arg Arg
385                 390                 395

<210> SEQ ID NO 13
<211> LENGTH: 412
<212> TYPE: PRT
<213> ORGANISM: homo sapiens

<400> SEQUENCE: 13

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ser Arg Gly Gln Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
290                 295                 300
```

His Asn Lys Cys Glu Cys Arg Pro Lys Asp Arg Ala Arg Gln Glu
305                 310                 315                 320

Lys Lys Ser Val Arg Gly Lys Gly Gln Lys Arg Lys Arg Lys
            325                 330                 335

Lys Ser Arg Tyr Lys Ser Trp Ser Val Tyr Val Gly Ala Arg Cys Cys
            340                 345                 350

Leu Met Pro Trp Ser Leu Pro Gly Pro His Pro Cys Gly Pro Cys Ser
            355                 360                 365

Glu Arg Arg Lys His Leu Phe Val Gln Asp Pro Gln Thr Cys Lys Cys
            370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 14
<211> LENGTH: 207
<212> TYPE: PRT
<213> ORGANISM: homo sapiens

<400> SEQUENCE: 14

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
            35                  40                  45

Pro Arg Glu Val Val Pro Leu Thr Val Glu Leu Met Gly Thr Val
        50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
            115                 120                 125

Lys Asp Ser Ala Val Lys Pro Asp Arg Ala Ala Thr Pro His His Arg
            130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
            195                 200                 205

<210> SEQ ID NO 15
<211> LENGTH: 188
<212> TYPE: PRT
<213> ORGANISM: homo sapiens

<400> SEQUENCE: 15

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Pro Leu Thr Val Glu Leu Met Gly Thr Val
50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Ser Pro Arg Pro Leu Cys Pro Arg
130                 135                 140

Cys Thr Gln His His Gln Arg Pro Asp Pro Arg Thr Cys Arg Arg Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
            180                 185

<210> SEQ ID NO 16
<211> LENGTH: 419
<212> TYPE: PRT
<213> ORGANISM: homo sapiens

<400> SEQUENCE: 16

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser

```
            195                 200                 205
Cys Arg Cys Met Ser Lys Leu Asp Val Tyr Arg Gln Val His Ser Ile
            210                 215                 220
Ile Arg Arg Ser Leu Pro Ala Thr Leu Pro Gln Cys Gln Ala Ala Asn
225                 230                 235                 240
Lys Thr Cys Pro Thr Asn Tyr Met Trp Asn Asn His Ile Cys Arg Cys
            245                 250                 255
Leu Ala Gln Glu Asp Phe Met Phe Ser Ser Asp Ala Gly Asp Asp Ser
            260                 265                 270
Thr Asp Gly Phe His Asp Ile Cys Gly Pro Asn Lys Glu Leu Asp Glu
            275                 280                 285
Glu Thr Cys Gln Cys Val Cys Arg Ala Gly Leu Arg Pro Ala Ser Cys
            290                 295                 300
Gly Pro His Lys Glu Leu Asp Arg Asn Ser Cys Gln Cys Val Cys Lys
305                 310                 315                 320
Asn Lys Leu Phe Pro Ser Gln Cys Gly Ala Asn Arg Glu Phe Asp Glu
            325                 330                 335
Asn Thr Cys Gln Cys Val Cys Lys Arg Thr Cys Pro Arg Asn Gln Pro
            340                 345                 350
Leu Asn Pro Gly Lys Cys Ala Cys Glu Cys Thr Glu Ser Pro Gln Lys
            355                 360                 365
Cys Leu Leu Lys Gly Lys Lys Phe His His Gln Thr Cys Ser Cys Tyr
370                 375                 380
Arg Arg Pro Cys Thr Asn Arg Gln Lys Ala Cys Glu Pro Gly Phe Ser
385                 390                 395                 400
Tyr Ser Glu Glu Val Cys Arg Cys Val Pro Ser Tyr Trp Lys Arg Pro
            405                 410                 415
Gln Met Ser

<210> SEQ ID NO 17
<211> LENGTH: 354
<212> TYPE: PRT
<213> ORGANISM: homo sapiens

<400> SEQUENCE: 17

Met Tyr Arg Glu Trp Val Val Asn Val Phe Met Met Leu Tyr Val
1               5                   10                  15
Gln Leu Val Gln Gly Ser Ser Asn Glu His Gly Pro Val Lys Arg Ser
            20                  25                  30
Ser Gln Ser Thr Leu Glu Arg Ser Glu Gln Ile Arg Ala Ala Ser
            35                  40                  45
Ser Leu Glu Glu Leu Leu Arg Ile Thr His Ser Glu Asp Trp Lys Leu
50                  55                  60
Trp Arg Cys Arg Leu Arg Leu Lys Ser Phe Thr Ser Met Asp Ser Arg
65                  70                  75                  80
Ser Ala Ser His Arg Ser Thr Arg Phe Ala Ala Thr Phe Tyr Asp Ile
            85                  90                  95
Glu Thr Leu Lys Val Ile Asp Glu Glu Trp Gln Arg Thr Gln Cys Ser
            100                 105                 110
Pro Arg Glu Thr Cys Val Glu Val Ala Ser Glu Leu Gly Lys Ser Thr
            115                 120                 125
Asn Thr Phe Phe Lys Pro Pro Cys Val Asn Val Phe Arg Cys Gly Gly
            130                 135                 140
Cys Cys Asn Glu Glu Ser Leu Ile Cys Met Asn Thr Ser Thr Ser Tyr
```

-continued

```
            145                 150                 155                 160
Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
                180                 185                 190

Pro Thr Ala Pro Arg His Pro Tyr Ser Ile Ile Arg Arg Ser Ile Gln
            195                 200                 205

Ile Pro Glu Glu Asp Arg Cys Ser His Ser Lys Lys Leu Cys Pro Ile
        210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
                260                 265                 270

Cys Lys Thr Pro Cys Pro Lys Asp Leu Ile Gln His Pro Lys Asn Cys
            275                 280                 285

Ser Cys Phe Glu Cys Lys Glu Ser Leu Glu Thr Cys Cys Gln Lys His
        290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
                340                 345                 350

Asn Pro
```